(12) United States Patent
Neal et al.

(10) Patent No.: US 9,008,786 B2
(45) Date of Patent: *Apr. 14, 2015

(54) DETERMINING STIMULATION SIGNALS FOR NEURAL STIMULATION

(75) Inventors: Tim Neal, West Ryde (AU); Bastiaan van Dijk, Mechelen (BE)

(73) Assignee: Cochlear Limited, Macquarie University, NSW (AU)

( * ) Notice: Subject to any disclaimer, the term of this patent is extended or adjusted under 35 U.S.C. 154(b) by 1464 days.

This patent is subject to a terminal disclaimer.

(21) Appl. No.: 12/260,983

(22) Filed: Oct. 29, 2008

(65) Prior Publication Data

US 2009/0177247 A1 Jul. 9, 2009

Related U.S. Application Data

(63) Continuation-in-part of application No. 11/451,349, filed on Jun. 13, 2006, now Pat. No. 8,285,382, which is a continuation-in-part of application No. 11/094,769, filed on Mar. 31, 2005, now Pat. No.
(Continued)

(30) Foreign Application Priority Data

Aug. 21, 2000 (AU) .................................. PQ9528

(51) Int. Cl.
*A61N 1/00* (2006.01)
*A61N 1/36* (2006.01)
(52) U.S. Cl.
CPC ......... *A61N 1/36032* (2013.01); *A61N 1/36146* (2013.01)

(58) Field of Classification Search
USPC ................ 607/55–57, 136–137; 381/312
See application file for complete search history.

(56) References Cited

U.S. PATENT DOCUMENTS

| | | |
|---|---|---|
| 4,441,202 A | 4/1984 | Tong et al. |
| 4,515,158 A | 5/1985 | Patrick et al. |
| 4,532,930 A | 8/1985 | Crosby et al. |
| 4,611,596 A | 9/1986 | Wasserman |
| 4,847,617 A | 7/1989 | Silvian |

(Continued)

FOREIGN PATENT DOCUMENTS

| | | |
|---|---|---|
| AU | 2005202733 | 1/2006 |
| EP | 0247649 | 12/1987 |

(Continued)

OTHER PUBLICATIONS

"Specialty Coating Systems: Rubber/Silicone", Specialty Coating Systems, (Webpage), www.scscoatings.com/1 parylene_applications/rubber-silicone.cfm, accessed via Internet Archive Wayback Machine (archive.org), available Nov. 24, 2005 (based on records of Internet Archive).

(Continued)

*Primary Examiner* — Catherine Voorhees
*Assistant Examiner* — Roland Dinga

(57) ABSTRACT

A tissue-stimulating prosthesis receives an input signal and determines a set of stimulation signals for use in generating electrical stimulation that will cause the recipient to perceive the input signal. The prosthesis determines a set of stimulation signals based on the perceptual power of at least one of the frequency components of the input signal or the perceptual power of one or more stimulation signals within the set.

30 Claims, 18 Drawing Sheets

Related U.S. Application Data 7,822,478, which is a continuation-in-part of application No. 10/343,397, filed as application No. PCT/AU01/01032 on Aug. 21, 2001, now Pat. No. 7,272,446.

(60) Provisional application No. 60/557,675, filed on Mar. 31, 2004, provisional application No. 60/616,216, filed on Oct. 7, 2004.

(56) References Cited

U.S. PATENT DOCUMENTS

| | | | |
|---|---|---|---|
| 5,046,242 | A | 9/1991 | Kuzma et al. |
| 5,271,397 | A * | 12/1993 | Seligman et al. ............ 607/137 |
| 5,274,711 | A | 12/1993 | Rutledge et al. |
| 5,403,262 | A | 4/1995 | Gooch |
| 5,412,748 | A | 5/1995 | Furuyama et al. |
| 5,601,617 | A | 2/1997 | Loeb et al. |
| 5,609,616 | A | 3/1997 | Schulman et al. |
| 5,626,629 | A | 5/1997 | Faltys et al. |
| 5,649,970 | A | 7/1997 | Loeb et al. |
| 5,653,742 | A | 8/1997 | Parker et al. |
| 5,687,282 | A | 11/1997 | Van De Kerkhof |
| 5,776,179 | A | 7/1998 | Ren et al. |
| 5,786,439 | A | 7/1998 | Van Antwerp et al. |
| 5,824,022 | A | 10/1998 | Zilberman et al. |
| 5,833,714 | A | 11/1998 | Loeb |
| 5,853,424 | A | 12/1998 | Rise |
| 5,895,416 | A | 4/1999 | Barreras, Sr. et al. |
| 5,909,497 | A | 6/1999 | Alexandrescu |
| 6,115,478 | A | 9/2000 | Schneider |
| 6,116,413 | A | 9/2000 | Tabor et al. |
| 6,198,971 | B1 | 3/2001 | Leysieffer et al. |
| 6,230,057 | B1 | 5/2001 | Chow et al. |
| 6,231,126 | B1 | 5/2001 | Cheng |
| 6,304,786 | B1 | 10/2001 | Heil, Jr. et al. |
| 6,304,787 | B1 | 10/2001 | Kuzma et al. |
| 6,321,126 | B1 | 11/2001 | Kuzma |
| 6,334,072 | B1 | 12/2001 | Leysieffer |
| 6,354,299 | B1 | 3/2002 | Fischell et al. |
| 6,366,863 | B1 | 4/2002 | Bye et al. |
| 6,421,569 | B1 | 7/2002 | Treaba et al. |
| 6,463,328 | B1 | 10/2002 | John |
| 6,497,729 | B1 | 12/2002 | Moussy et al. |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,594,525 | B1 | 7/2003 | Zierhofer et al. |
| 6,697,674 | B2 | 2/2004 | Leysieffer et al. |
| 6,751,505 | B1 | 6/2004 | Van Den Honert et al. |
| 6,778,040 | B2 | 8/2004 | Kim et al. |
| 6,778,858 | B1 * | 8/2004 | Peeters ............................ 607/57 |
| 6,879,693 | B2 | 4/2005 | Miller et al. |
| 6,916,291 | B2 | 7/2005 | Givens et al. |
| 7,171,272 | B2 | 1/2007 | Blamey et al. |
| 7,181,297 | B1 | 2/2007 | Pluvinage et al. |
| 7,218,971 | B2 | 5/2007 | Heil, Jr. et al. |
| 7,251,530 | B1 | 7/2007 | Overstreet et al. |
| 7,272,446 | B2 | 9/2007 | Parker et al. |
| 7,317,944 | B1 | 1/2008 | Overstreet |
| 7,328,151 | B2 | 2/2008 | Muesch |
| 7,822,478 | B2 | 10/2010 | Killian et al. |
| 8,050,770 | B2 | 11/2011 | Parker et al. |
| 2001/0050837 | A1 | 12/2001 | Stevenson et al. |
| 2002/0176584 | A1 | 11/2002 | Kates |
| 2003/0109903 | A1 | 6/2003 | Berrang et al. |
| 2003/0199950 | A1 | 10/2003 | Stolz et al. |
| 2003/0233133 | A1 | 12/2003 | Greenberg et al. |
| 2004/0098063 | A1 | 5/2004 | Goetz |
| 2004/0127968 | A1 | 7/2004 | Kuzma et al. |
| 2004/0147992 | A1 | 7/2004 | Bluger et al. |
| 2006/0004432 | A1 | 1/2006 | Parker et al. |
| 2006/0235490 | A1 | 10/2006 | Killian et al. |
| 2007/0127745 | A1 | 6/2007 | Gibson et al. |
| 2009/0204177 | A1 | 8/2009 | Parker et al. |
| 2009/0292161 | A1 | 11/2009 | Parker |

FOREIGN PATENT DOCUMENTS

| | | |
|---|---|---|
| EP | 0282336 | 9/1988 |
| EP | 0124930 | 6/1990 |
| JP | 61001200 | 1/1986 |
| JP | 63242252 | 10/1988 |
| JP | 8501241 | 2/1996 |
| JP | 10508442 | 8/1998 |
| JP | 11-513539 T | 11/1999 |
| JP | 2000509566 | 7/2000 |
| WO | 9324176 | 12/1993 |
| WO | 9501709 | 1/1995 |
| WO | 9612383 | 4/1996 |
| WO | WO-9626673 | 9/1996 |
| WO | 9709863 A1 | 3/1997 |
| WO | 97/43871 A1 | 11/1997 |
| WO | 97/48447 | 12/1997 |
| WO | 9965276 | 12/1999 |
| WO | 0103622 | 1/2001 |
| WO | 0119304 | 3/2001 |
| WO | 0199470 | 12/2001 |
| WO | WO-0217679 | 2/2002 |

OTHER PUBLICATIONS

Japanese Patent Application No. 2002-561453, Notice of Reasons for Rejection dated Jun. 16, 2009. (English Translation).
CA Examiner's report dated May 29, 2007.
Nogueira et al. "A Psychoacoustic 'NofM'-Type Speech Coding Strategy for Cochlear Implants," EURASIP Journal on Applied Signal Processing, pp. 3044-3059, 2005.
Supplementary European Search Report dated Aug. 11, 2005.
First European Examiner's Report for European Application No. 01959971.1 dated dated Nov. 23, 2005.
Second CA Office Action dated Dec. 10, 2008.
Bernd Edler, Heiko Purnhagen, and Charalampos Ferekidis, ASAC—Analysis/Synthesis Audio Codec For Very Low Bill Rates, 100th AES Convention, Copenhagen (May 1996).
Frank Baumgarte, Charalampos Ferekidis, and Hendrik Fuchs, A Nonlinear Psychoacoustic Model Applied to the ISO MPEG Layer 3 Coder, 99th AES Convention, New York (Oct. 1995).
Lawrence T. Cohen, Louise M. Richards, Elaine Saunders, and Robert S.C. Cowen, Spatial Spread of Neural Excitation in Cochlear Implant Recipients: Comparison of Improved ECAP Method and Psychophysical Forward Masking, 179 Hearing Res. 72-87 (May 2003).
Abbas PJ, Brown CJ, Hughes ML, Ganz BJ, Wolaver AA, Gervais JP and Hong SH, Electrically evoked compound action potentials recorded from subjects who use the nucleus C124M device, 185 Ann Otol Rhinol Laryngol Suppl. 6-9 (Dec. 2000).
Lawrence T. Cohen, Elaine Saunders, and Louise M. Richardson, Spatial Spread of Neural Excitation: Comparison of Compund Action Potential and Forward-Masking Data in Cochlear Implant Recipients, 43 International Journal of Audiology.
Miller CA, Abbas PJ, Brown CJ, An Improved Method of Reducing Stimulus Artifact in the Electrically Evoked Whole Nerve Potential 21(4) Ear Hear 280-90 (Aug. 2000).
International Search Report dated Oct. 5, 2001; counterpart patent application PCT/AU01/01032 filed Aug. 21, 2001; Publication No. WO 02/17679; Publication Date Feb. 28, 2002: Inventors: John Parker et al.: Applicant Cochlear Limited.
International Preliminary Examination Report dated Apr. 10, 2002; counterpart patent application PCT/AU01/01032 filed Aug. 21, 2001; Publication No. WO 02/17679; Publication Date Feb. 28, 2002: Inventors: John Parker et al.: Applicant Cochlear Limited.
Supplemental European Search Report dated Aug. 11, 2005.

* cited by examiner

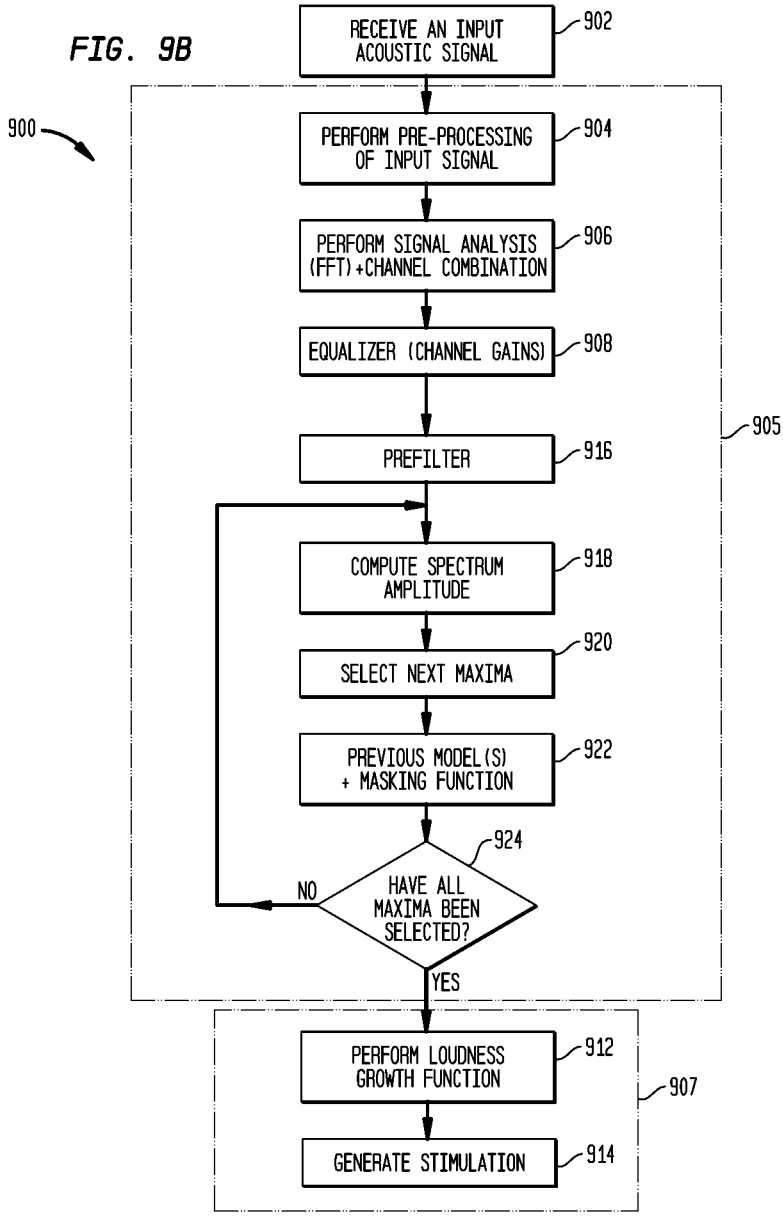

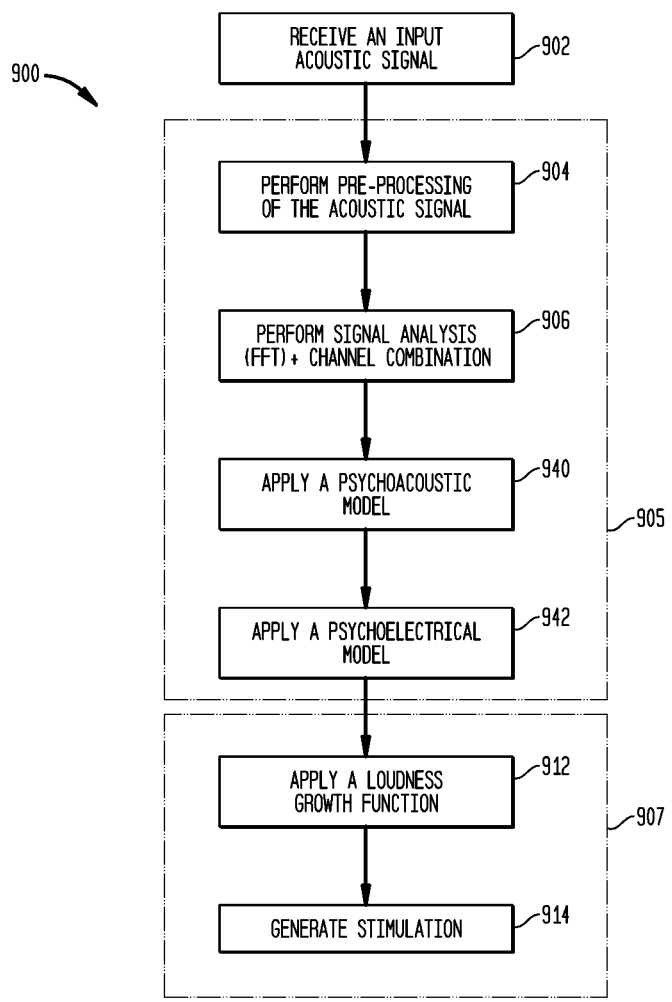

DETERMINING STIMULATION SIGNALS FOR NEURAL STIMULATION

CROSS-REFERENCE TO RELATED APPLICATIONS

This application is a continuation-in-part of U.S. patent application Ser. No. 11/451,349, filed Jun. 13, 2006, entitled "Determining Stimulation Signals For Neural Coding," which is a continuation-in-part of U.S. application Ser. No. 11/094,769, filed Mar. 31, 2005, entitled "Compressed Neural Coding," which is a continuation-in-part of application Ser. No. 10/343,397, filed Feb. 21, 2003, entitled "Power Efficient Electrical Stimulation," now U.S. Pat. No. 7,272,446, which is a national stage of PCT application PCT/AU01/01032, filed Aug. 21, 2001, which claims priority to Australian Patent Application No. PQ9528 filed Aug. 21, 2000. This application also claims the benefit of the following U.S. provisional applications: U.S. Provisional Application No. 60/557,675, entitled "Spread of Excitation and MP3 Coding," filed Mar. 31, 2004; and U.S. Provisional Application No. 60/616,216, entitled "Spread of Execution and Compressed Audible Speech Coding," filed Oct. 7, 2004. This application is related to commonly owned and co-pending U.S. patent application Ser. No. 11/857,253, filed Sep. 18, 2007, entitled "Power Efficient Electrical Stimulation." The above applications are hereby incorporated by reference herein.

This application also makes reference to the following U.S. patent applications: U.S. application Ser. No. 10/478,675, entitled "A Peak-Derived Timing Stimulation Strategy for a Multi-Channel Cochlear Implant," filed Nov. 24, 2003, now U.S. Pat. No. 7,310,558; U.S. Application No. 60/548,104, entitled "Rotable Belt Clip for Body-Worn Speech Processor," filed Feb. 27, 2004; U.S. Application No. 60/548,094, entitled "Reversible Belt Clip for Body-Worn Speech Processor," filed Feb. 27, 2004; U.S. application Ser. No. 10/798,847, entitled "Virtual Wire Assembly having Hermetic Feedthroughs," filed Mar. 12, 2004, now U.S. Pat. No. 7,174,223; and U.S. Application No. 60/557,713 "Ramping Pulse Train Stimulation," filed Mar. 31, 2004. The above applications and patents are hereby incorporated by reference herein.

BACKGROUND

1. Field of the Invention

The present invention relates generally to neural stimulation, and more particularly, to determining stimulation signals for neural stimulation.

2. Related Art

Certain medical devices, sometimes referred to as tissue-stimulating prosthesis, operate by delivering an electrical stimulation to a recipient. These prostheses include, but are not limited to, cardiac pacemakers, neural stimulators, prosthetic hearing implant systems, and the like. Tissue-stimulating prostheses, which are typically reliant upon stored power, share a common dynamic. As the possible and desired functionality of the devices is improved, the power demands generally increase. As a result, the life per charge or per battery cell is reduced. This not only raises costs for the user (also referred to herein as the patient, wearer and recipient; collectively and generally referred to herein as "recipient"), it also increases the risk that a device will cease operating at an inconvenient time due to loss of power.

Prosthetic hearing implant systems, such as auditory brain stimulators and Cochlear™ implants (also commonly referred to as Cochlear™ implant devices, Cochlear™ prostheses, and the like; simply "cochlear implant" herein), are generally used to treat sensorineural hearing loss. Sensorineural hearing loss is due to the absence of, or destruction of, the hair cells in the cochlea which transduce acoustic signals into nerve impulses. Prosthetic hearing implant systems bypass the hair cells in the cochlea and directly deliver electrical stimulation to the auditory nerve fibres, thereby allowing the brain to perceive a hearing sensation resembling the natural hearing sensation normally delivered to the auditory nerve.

Prosthetic hearing systems generally include a sound processor that converts sound into a coded signal. Traditionally, during processing, a sound is decomposed into frequency bands or channels based on the "spectral power" rather than the "perceptual power" of the frequency band. The spectral power of a frequency band is the relative physical amplitude of the frequency components in the band in terms of, for example, sound pressure level. That is, the spectral power of a frequency band is an objective measure of the power level within a band. In contrast, perceptual power identifies how important a frequency component is for the perception of the sound. The traditional decomposition based on spectral power is used in current speech processing strategies of commercially available cochlear implants.

The coded signal output by the sound processor is provided to a stimulator unit situated within a recess of the temporal bone of the recipient. The stimulator unit processes the coded signal and outputs signals to an intracochlea electrode assembly which applies electrical stimulation directly to the recipient's auditory nerve, thereby producing a hearing sensation corresponding to the original detected sound.

The presence of such an electrical stimulus on one electrode may prevent or change the detection of signals delivered via other electrodes. This effect is called masking. By considering the masking effect it is therefore possible to classify signals that will not be accurately perceived by the recipient as unnecessary.

SUMMARY

In one aspect of the invention, a method of providing neural stimulation to a recipient with a tissue-stimulating prosthesis is disclosed. The method comprises: receiving an input signal; determining a set of stimulation signals corresponding to the input signal in which the amplitude of at least one stimulation signal is adjusted based on the perceptual power of at least one other signal within the set; and delivering the determined set of stimulation signals to the recipient.

In another aspect of the present invention, a method of providing neural stimulation to a recipient with a tissue-stimulating prosthesis having a plurality of channels for delivery of electrical stimulation signals is provided. The method comprises: receiving an input signal; generating stimulation signals corresponding to frequency components of the input signal; using the perceptual power of frequency components of the input signal to select channels of the tissue-stimulating prosthesis for delivery of the generated stimulation signals to the recipient; and delivering the generated stimulation signals to the recipient via the selected channels.

BRIEF DESCRIPTION OF THE DRAWINGS

Embodiments of the present invention are described herein in conjunction with the accompanying drawings, in which:

FIG. 9B is detail level flowchart illustrating the operations performed during a method in accordance with one embodiment of FIG. 9A;

FIG. 9F is detail level flowchart illustrating the operations performed during a method in accordance with one embodiment of FIG. 9A;

DETAILED DESCRIPTION

Embodiments of the present invention are generally directed to determining stimulation signals for neural stimulation of a recipient. A tissue-stimulating prosthesis receives an input signal and determines a set of stimulation signals for use in generating electrical stimulation that will cause the recipient to perceive the input signal.

In one aspect of the present invention, the tissue-stimulating prosthesis identifies signals within the determined stimulation set which are likely be masked upon delivery of the electrical stimulation signals to the recipient. The tissue-stimulating prosthesis identifies these likely masked signals based on the perceptual power of at least one signal in the set. The tissue-stimulating prosthesis scales the likely masked signals to adjust for masking resulting from the at least one signal. The tissue-stimulating prosthesis then delivers the stimulation signals to the recipient.

In another aspect of the present invention, the tissue-stimulating prosthesis determines a set of stimulation signals based on the perceptual power of an input signal. The prosthesis comprises a plurality of channels for delivery of stimulation signals to the recipient, each channel terminating in an electrode. Frequency components of the input signal having the highest perceptual power are used to select channels of the prosthesis for delivery of stimulation signals to the recipient. Certain channels are deemphasized such that signals will likely be chosen for delivery of stimulation signals. Stimulation signals are then delivered to the recipient via selected and/or non-deemphasized channels.

Embodiments of the present invention are described herein primarily in connection with one type of tissue-stimulating prosthesis, a prosthetic hearing implant system. Prosthetic hearing implant systems include but are not limited to auditory brain stimulators and Cochlear™ implants (also commonly referred to as Cochlear™ implant devices, Cochlear™ prostheses, and the like; simply "cochlear implant" herein).

Figure 1:
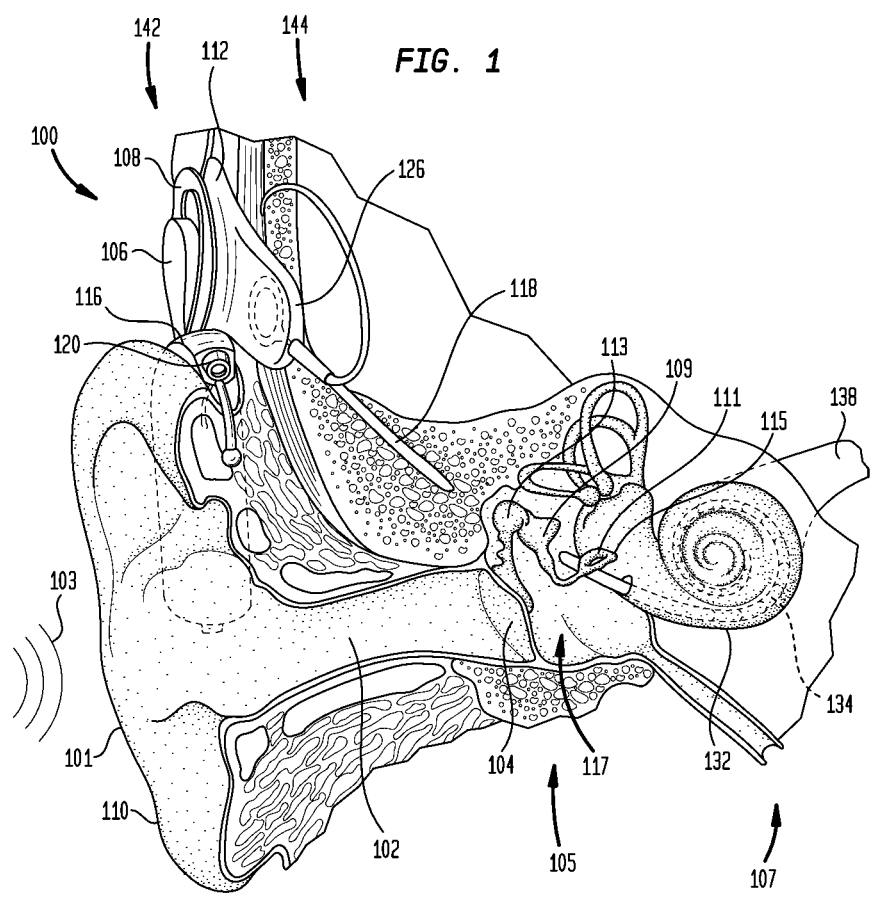
FIG. 1 is a schematic diagram of one embodiment of an exemplary prosthetic hearing device, a cochlear implant, suitable for implementing embodiments of the present invention.

FIG. 1 is a perspective view of an exemplary prosthetic hearing implant system, namely a cochlear implant system 100, in which embodiments of the present invention may be implemented. The relevant components of outer ear 101, middle ear 105 and inner ear 107 are described next below. An acoustic pressure or sound wave 103 is collected by outer ear 101 (e.g., the auricle) and channeled into and through ear canal 102. Disposed across the distal end of ear canal 102 is a tympanic membrane 104 which vibrates in response to acoustic wave 103. This vibration is coupled to oval window or fenestra ovalis 115 through three bones of middle ear 105, collectively referred to as the ossicles 117 and comprising the malleus 113, the incus 109 and the stapes 111. Bones 113, 109 and 111 of middle ear 105 serve to filter and amplify acoustic wave 103, causing oval window 115 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells (not shown) and auditory nerve 138 to the brain (not shown), where they are perceived as sound.

Cochlear prosthesis 100 comprises external component assembly 142 which is directly or indirectly attached to the body of the recipient, and an internal component assembly 144 which is temporarily or permanently implanted in the recipient. External assembly 142 typically comprises microphone 120 for detecting sound, a speech processing unit 116, a power source (not shown), and an external transmitter unit 106. External transmitter unit 106 comprises an external coil 108 and, preferably, a magnet (not shown) secured directly or indirectly to the external coil 108. Speech processing unit 116 processes the output of microphone 120 that is positioned, in the depicted embodiment, by ear 110 of the recipient. Speech processing unit 116 generates coded signals, referred to herein as a stimulation data signals, which are provided to external transmitter unit 106 via a cable (not shown). Speech processing unit 116 is, in this illustration, constructed and arranged so that it can fit behind outer ear 101 (e.g., the auricle). Alternative versions may be worn on the body or it may be possible to provide a fully implantable system which incorporates the speech processor and/or microphone into the internal component assembly 144.

Internal components 144 comprise an internal receiver unit 112, a stimulator unit 126 and an electrode assembly 118. Internal receiver unit 112 comprises an internal transcutaneous transfer coil (not shown), and preferably, a magnet (also not shown) fixed relative to the internal coil. Internal receiver unit 112 and stimulator unit 126 are hermetically sealed within a biocompatible housing. The internal coil receives power and data from external coil 108, as noted above. A cable or lead of electrode assembly 118 extends from stimulator unit 126 to cochlea 132 and terminates in an array 134 of electrodes. Signals generated by stimulator unit 126 are applied by the electrodes of electrode array 134 to cochlear 132, thereby stimulating the auditory nerve 138.

In one embodiment, external coil 108 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 112 may be positioned in a recess of the temporal bone adjacent to ear 110 of the recipient.

Further details of the above and other exemplary prosthetic hearing implant systems in which embodiments of the present invention may be implemented include, but are not limited to, those systems described in U.S. Pat. Nos. 4,532,930, 6,537,200, 6,565,503, 6,575,894 and 6,697,674, which are hereby incorporated by reference herein in their entireties. For example, while cochlear prosthesis 100 is described as having external components, in alternative embodiments, cochlear prosthesis 100 may be a totally implantable prosthesis. In one exemplary implementation, for example, speech processing unit 116, including the microphone, speech processor and/or power supply may be implemented as one or more implantable components. In one particular embodiment, speech processing unit 116 may be contained within the hermetically sealed housing used for speech processing unit 116.

In both normal hearing as well as in hearing as a response to electrical stimulation, sometimes referred to as electrical hearing, the presence of a signal can prevent or change the detection of other signals that are also present in the spectrum, this effect is called masking. Embodiments of the present invention use this masking phenomenon to, for example, reduce power consumption or reduce processing in a prosthetic hearing device. As noted above, cochlear implant 100 receives an input signal. This input signal may comprise an acoustic signal received at microphone 120, or an electrical signal received via an electrical input (not shown). Such an electrical input receives electrical sound signals directly from an external device, such as, for example, FM hearing systems, MP3 players, televisions, etc. The input signal may also be received via a telecoil (also not shown) which permits cochlear implant 100 to connect to a telephone or other similar device. Using the input signal, cochlear implant 100 determines a set of stimulation signals which will produce a hearing perception corresponding to the input signal.

In one embodiment, one or more stimulation signals within this stimulation set which are likely to be masked upon delivery of the stimulation signals to the recipient are adjusted based on the perceptual power of one or other stimulation signals within the set. In an alternative embodiment, the set of stimulation signals are determined based on the perceptual power of the input signal. Specifically, the frequency components of the input signal having the largest perceptual power are identified and stimulation signals corresponding to these components are included in the stimulation set. In either case, cochlear implant 100 delivers the determined electrical stimulation signals to the recipient. This allows cochlear implant 100 to deliver to the recipient stimulation signals having greater, and preferably the highest, perceptual power, rather than delivering stimulation signals having the highest spectral power, when stimulating auditory nerve 138.

Determination of the set of stimulation signals may make use of one or more estimations of masking which is likely to occur when a given electrical stimulation is delivered to the recipient. In certain embodiments, these masking estimations may be developed using various models, such as psychoacoustical masking models (for estimation of the masking effects in normal hearing) and psychoelectric masking models (to estimate the masking effect in electric hearing). Such models may be based on the psychoacoustic and/or psychoelectric characteristics of an individual recipient, a defined population of individuals, etc.

For ease of discussion, we will use the following two terms in the following discussion: spectral power, and perceptual power. Classically, if a complex sound is decomposed into frequency bands or channels, one can compare the relative 'importance' of each band by looking at the relative physical amplitudes in terms of, for example, sound pressure level. This relative physical amplitude is referred to herein as the "spectral power" of the frequency band. The selection of maxima based on highest spectral powers is used in current speech processing strategies of commercially available cochlear implants such as Speak and ACE. However, because spectral power is purely a physical measure, it does not take into account a recipient's actual perception of a delivered signal. For example, a tone that is above the maximum audible frequency may have very high spectral power but still be inaudible and thus will not be perceived by a normal hearing listener. To identify how important a frequency component is for the perception of the sound, the term 'perceptual power' is used herein to refer to the actual contribution of that component to perception. For example, the above mentioned tone that is outside the audible frequency range may have high spectral power, but will have no perceptual power. As described below, embodiments of the present invention use the perceptual power of a stimulation signal as the basis for determining masking estimations.

In one embodiment of the present invention, the cochlear implant uses a psychophysical model such as, for example, a psychoacoustic model or a psychoelectric model to estimate likely masking. As used herein, psychoacoustic and psychoelectric models are mathematical models of the masking properties of the human auditory system. A "psychoelectric model" is concerned with electrical stimuli (e.g., pulse bursts) on electrodes, while a psychoacoustical model relates to acoustical stimulation of the normal ear. As used herein, the term psychoelectric model refers to any model concerned with electrical stimuli of electrodes, including both user-specific models and models for a population of implant recipients, including for example, all implant recipients or a population of implant recipients sharing a common characteristic.

The term "psychoacoustic model" as used herein refers to a model that models a population of normal hearing persons. This population may be, for example, for all normal hearing persons as a whole, or for a group of persons, sharing a common characteristic (e.g., elderly persons with reduced hearing, children, females, etc.). Exemplary psychoacoustic models include, for example, the MPEG-1 Psychoacoustic Model 1, and the MPEG-2 Psychoacoustic Model 2.

A more detailed description of exemplary psychoacoustic models can be found in Bernd Edler, Heiko Purnhagen, and Charalampos Ferekidis, *ASAC—Analysis/Synthesis Audio Codec for Very Low Bit Rates,* 100th AES Convention, Copenhagen (May 1996); and Frank Baumgarte, Charalampos Ferekidis, and Hendrik Fuchs, *A Nonlinear Psychoacoustic Model Applied to the ISO MPEG Layer 3 Coder,* 99th AES Convention, New York, October (hereinafter "the Baumgarte reference"), both of which are hereby incorporated by reference herein.

In some embodiments, the models may be very complicated and may model many explicit characteristic of the stimulated auditory nerve. In alternative embodiments, as described in greater detail below, the models may be a very simple scheme, such as, one wherein channels neighboring a channel which is to deliver electrical stimulation, referred to as the masking channel, are automatically deemed masked. Stimulation signals delivered via these masked channels are then scaled to account for the masking caused by the masking channel. This simplified scheme is sometimes referred to as an N+X scheme, where X represents the number of neighboring channels that are to be deemed masked. For example, an N+1 scheme would result in the scaling of signals delivered via channels immediately on either side of the selected channel. In another example, an N+2 scheme would result in the scaling of stimulation signals delivered via the 2 channels closest to each side of the selected channel. The number of channels masked by a selected channel may be asymmetric about the selected channel such that, for example, one channel to the left and two channels to the right of the selected channel are scaled.

As noted, masking models may be used in certain embodiments of the present invention. These masking models may be expressed in sound pressure level (dBSPL) versus frequency or in stimulating current versus electrode number or channel number. These different representations of the same process can be interchanged and calculated from one to another and back again. It will be clear to somebody skilled in the art that this transformation arises uniquely from the processing path used. For ease in explanation, the term "input-referred psychoelectric model" is used herein to refer to a psychoelectric model that is in terms of sound pressure level (expressed in decibels relative to 20 µPa (dBSPL) versus frequency (in terms of Hertz (Hz)). That is, an input-referred psychoelectric model is a model that is concerned with electrical stimuli of electrodes, but is in terms of sound pressure level (dBSPL) versus frequency (Hz). In contrast, a psychoelectric model in terms of microvolts (or current level) versus electrode number is referred to as an output-referred psychoelectric model because the model would be defined in terms of an output quantity of the system. In a cochlear prosthesis such as cochlear prosthesis 100 described above, the individual or combinations of neighboring electrodes of electrode array 134 correspond to different frequency bands, and as such, in principal an output-referred psychoelectric model can be translated into an input-referred psychoelectric model, and vice versa. That is, there is a one-to-one relationship between stimulation current on a specific electrode and acoustical energy present in the spectral band belonging to that electrode. For clarity, the term "psychoelectric model" will be used hereinafter to refer to both output-referred psychoelectric models as well as input-referred psychoelectric models.

Figure 2:
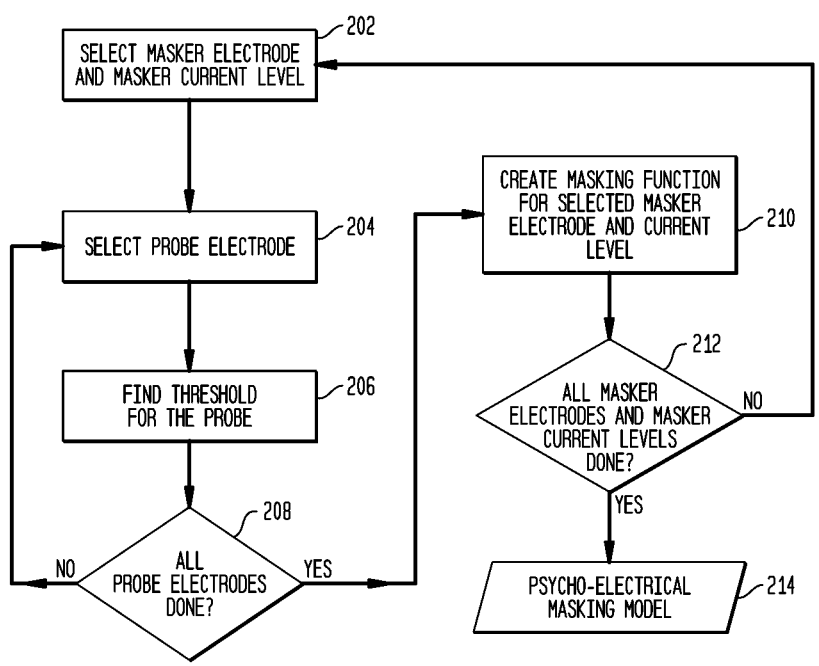
FIG. 2 illustrates a simplified flow chart of an exemplary method for generating a psychoelectric masking model, in accordance with one embodiment of the present invention.

FIG. 2 illustrates a simplified flow chart of a method for generating a psychoelectric masking model in accordance with one embodiment of the present invention. FIG. 2 will be described with reference to FIG. 1 where electrode array 134 includes a plurality of electrodes (for example, 22 electrodes). In the following description, two types of electrodes are referenced depending on the effect of their operation: masker electrodes and probe electrodes. A probe electrode is an electrode (or frequency in an input-referred psychoelectric model) that is used to probe the amount of masking; the masker electrode is an electrode (or frequency in an input-referred psychoelectric model) that potentially masks the probe electrode.

Initially at block 202, one of the electrodes of electrode array 134 is selected as the masker electrode and a current level is determined for stimulating the masker electrode. The current level for stimulating the masker electrode may be, for example, set as the Maximum Comfort Level (C-level) for the masker electrode, or some value below the C-level but greater than the Threshold current level (T-level) for the masker electrode. It should be appreciated that in alternative embodiments, the selected current level for the masker electrode may initially be below the T-level for the masker electrode.

Next, an electrode of electrode array 134 is selected as the probe electrode at block 204. The threshold for this probe electrode given the previously selected masker electrode and masker current level is determined at block 206. The threshold is the threshold current level for the probe electrode where stimulation for the probe electrode first becomes audible to the implant recipient in the presence of stimulation by the masker electrode at the masker current level. In psychoacoustics, this threshold is commonly referred to as a masked detection threshold.

In this example, the threshold may be determined by sequentially stimulating the masker electrode followed by the probe electrode. This technique is referred to herein as forward masking. In other embodiments, a backward masking technique may be used where the probe electrode is stimulated prior to the masker electrode. In other embodiments, the probe and masker electrodes are stimulated simultaneously, a technique referred to herein as simultaneous masking.

In determining the threshold, the probe current level (PCL) may initially be set at a low level and then be gradually increased until the implant recipient can hear the probe sound. The implant recipient may indicate whether or not they can hear any sound from the probe electrode by, for example, pressing down a button if they hear the sound and releasing it if the sound becomes inaudible. A further description of techniques for measurement of psychophysical forward masking is provided in Lawrence T. Cohen, Louise M. Richards, Elaine Saunders, and Robert S. C. Cowen, *Spatial Spread of Neural Excitation in Cochlear Implant Recipients Comparison of Improved ECAP Method and Psychophysical Forward Masking,* 179 Hearing Res. 72-87 (May 2003) (hereinafter "the Cohen et al. 2003 paper"), which is hereby incorporated by reference herein.

After the threshold for this combination of masker and probe electrode is determined, it is next determined at block 208 whether other probe electrodes should be tested and their thresholds determined. Preferably the detection threshold for every combination of masker electrode and probe electrode is determined. Thus, if there are more probe electrodes for which to determine a threshold for this particular masker electrode, the process returns to block 204 and a next probe electrode is selected at block 204 and the operation performed at block 206 is performed for this combination of masker and probe electrodes.

After the thresholds for the probe electrodes of electrode array 134 are determined, a masking function for this masker electrode and masker current level is determined at block 210. A further description of exemplary techniques for determining masking functions is provided in the above-referenced Cohen et al. 2003 reference.

Next, at block 212 it is determined whether all masker electrodes and masker current levels have been selected. If not, the process returns to block 202 and the above operations are repeated for another masker electrode. If so, the psychoelectric masking model is determined at block 214 by combining the above-described masking functions. The measurements obtained in determining a psychoelectric model are hereinafter referred to as psychoelectric measurements.

The above psychoelectric measurements comprise a set of masking functions for different current levels for all electrodes available in electrode array 134. A masking function for a given electrode at a given current level is defined by masking thresholds (in current level or CL) for all electrodes in electrode array 134. As noted above, this output-referred psychoelectric model may be translated, if desired, to an input-referred psychoelectric model so that instead of being in terms of CLs, it is in terms of sound pressure level (for example, dBSPL) and vice versa. Additionally, rather than being in terms of electrodes, the measurements may also be translated so that they are in terms of the center frequencies of the frequency bands corresponding to the electrodes in array 134, and visa versa. The resulting masking model may then be used when taking masking effects into account when determining the stimulation signals to be used for stimulating electrode array 134, such as is described in further detail below.

Additionally, in another example, a psychoelectric model that is determined in terms of sound pressure levels (dBSPL) (that is, an input-referred psychoelectric model) can be translated into a psychoelectric model in terms of current levels. This may be accomplished by, for example, using a loudness growth function, such as, for example, a loudness growth function that is in terms of dB on one axis (the x-axis) and in terms of % CL on the other axis (Y-axis), where 100% CL represents the current level corresponding to the maximum point on the measurement curve. Additionally, this loudness growth function may, for example, be adapted for the implant recipient, and parameters, such as, for example, its steepness (Q-factor) may be adapted according to feedback from the implant recipient. As one of ordinary skill in the art would appreciate, it is not necessary to translate current level back to dBSPL nor to translate electrode back to frequency, or vice versa. In alternative embodiments the values of either the psychoelectric model in terms of dBSPL, current levels, or, for example, micro-volts may be used when taking masking effects into account when selecting stimulation signals, as is described in further detail below.

As noted above, a cochlear implant uses a number of steps to calculate the stimulation current from the input sound level, such as, for example, filtering, selection, and loudness mapping (i.e., translating the acoustical energy into electrical current delivered to the electrodes). As one of ordinary skill in the art would appreciate; knowing the path that is used to translate acoustical to electrical parameters would allow for translation of the psychoacoustical model into the electric domain.

In addition to the above-noted method for determining psychoelectrical models, in other embodiments, other mechanisms may be used. For example, the above-described method of FIG. 2 may be adapted for determining a psychoelectrical model using electrophysiological measurements. In such an example, rather than determining a detection threshold using psychophysical measurements at block 206, the method determines the masking threshold based on electrophysiological measurements. These electrophysiological measurements may include, for example, measuring Electrical Compound Action Potentials (ECAP) of the auditory nerve, Electrically Evoked Auditory Brainstem Potentials (EABP) or Cortically Evoked Potentials (CEP). A more detailed description of exemplary methods for determining an electrophysiological model for use by a cochlear prosthesis is provided below.

In one embodiment, the cochlear prosthesis is a Nucleus® 24 cochlear implant system or a Nucleus® Freedom™ cochlear implant system, both of which are commercially available from Cochlear Limited, Australia. (NUCLEUS is a registered trademark and FREEDOM is a trademark of Cochlear Limited.) In such systems, electrode array 134 includes a plurality of electrodes (e.g., 22). Further, in this example, cochlear prosthesis 100 includes a version of Cochlear's Neural Response Telemetry (NRT™) software, such as, for example, Custom Sound EP™ software. (NRT and EP are trademarks of Cochlear Limited.) The NRT™ software and the Custom Sound EP™ software can be used to record ECAP potentials of the auditory nerve 138 in Nucleus™ 24 or Nucleus Freedom™ implant recipients. Further, a subtraction method may be used to minimize the stimulation artifact. For example, electrophysiological measurements measure nerve tissue potentials. The amplitudes of these potentials are typically in the 1-500 microvolt range and may be evoked by electrical stimuli that create an artifact that may by up to 10000 times larger than the response that is trying to be measured. Thus, a subtraction technique, such as discussed above may be used to minimize this artifact. A detailed description of a suitable subtraction method can be found in Abbas P J, Brown C J, Hughes M L, Ganz B J, Wolayer A A, Gervais J P and Hong S H, *Electrically evoked compound action potentials recorded from subjects who use the nucleus C124M device*, Ann Otol Rhinol Laryngol Suppl. 2000 December; 185:6-9 (hereinafter "the Abbas et al 2000 paper"), which is hereby incorporated by reference herein.

A further description of masker and probe stimuli and their use in determining spread of excitation (SOE) curves for an implant recipient is provided in the above-referenced Cohen et al. 2003 paper and Lawrence T. Cohen, Elaine Saunders, and Louise M. Richardson, *Spatial Spread of Neural Excitation: Comparison of Compound Action Potential and Forward-Masking Data In Cochlear Implant Recipients*, 43 International Journal of Audiology 346-355 (2004), (hereinafter "the Cohen et al. 2004 paper"), which is hereby incorporated by reference herein.

Spread of excitation may, amongst other ways, be determined by varying the recording electrode. The recording electrode is the electrode used to take the electrophysiological measurements (e.g., ECAP) and may be any of the electrodes of electrode array 134. Additionally, the measured response typically decreases in amplitude as the recording electrode is moved away from the masker/probe electrode.

The subtraction method (described elsewhere herein with reference to the Abbas et al. 200 paper) and the "Masked Response Extraction technique" (also sometimes referred to as the "Miller technique") can also be used to create spread of excitation curves. The "Masked Response Extraction technique" (aka "Miller technique") is described in Miller C A, Abbas P J, Brown C J, *An Improved Method of Reducing Stimulus Artifact in the Electrically Evoked Whole Nerve Potential*, 21(4) Ear and Hearing 280-90 (August 2000), which is hereby incorporated by reference herein. A further description and comparison of mechanisms for generating SOE curves from ECAP measurements is provided in the above-referenced Cohen et al. 2003 paper and Cohen et al. 2004 paper.

Figure 3:
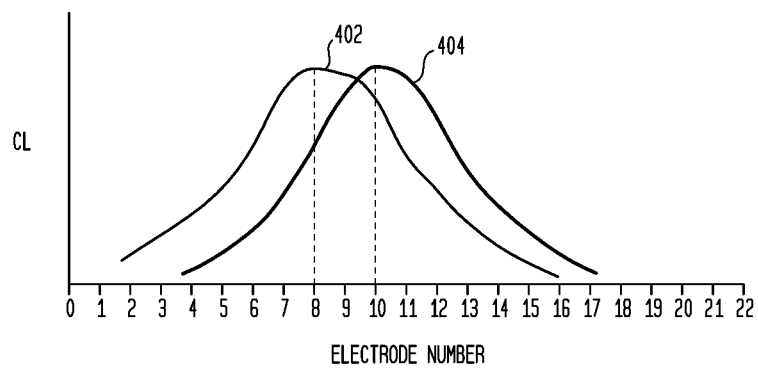
FIG. 3 illustrates a conceptual diagram of overlapping spread of excitations for a masker and a probe, in accordance with one embodiment of the present invention.

Additionally, in another embodiment, to determine the electrophysiological model, the masker and probe electrode need not be the same electrode, but instead may also be different electrodes. In such an example, cochlear prosthesis 100 may include Cochlear's NRT™ software. In this example, when the masker electrode is close to (or the same as) the probe electrode, the masking effect will be at a maximum, and as the masker and probe electrode get further apart the amount of the masking will decrease. For example, FIG. 3 illustrates a conceptual diagram of overlapping spread of excitations where the probe electrode is the $8^{th}$ electrode and the masker electrode is the $10^{th}$ electrode of electrode array 134. As illustrated, both the probe excitation field 402 and masker excitation field 404 overlap, thus indicating that there is substantial masking. This overlap may then be measured and used to generate an SOE curve.

Figure 4:
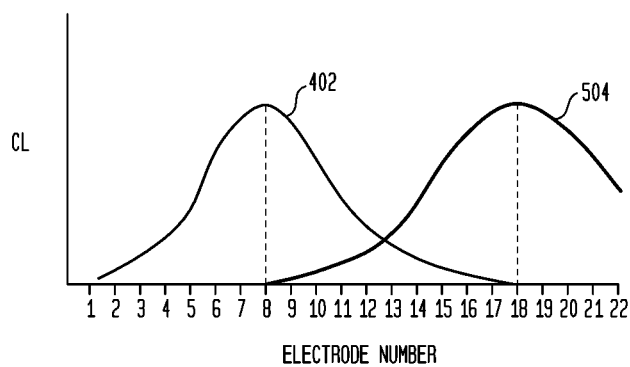
FIG. 4 illustrates a conceptual diagram of overlapping spread of excitations for a masker and a probe, in accordance with one embodiment of the present invention.

FIG. 4 illustrates a conceptual diagram of the overlapping spread of excitations where the probe electrode is still the $8^{th}$ electrode, but the masker electrode has been changed to the $18^{th}$ electrode. As illustrated, the masker's excitation field 504 and the probe's excitation field 402 slightly overlap. Together, FIGS. 3 and 4 illustrate that although there is still some masking where the masker electrode was the $18^{th}$ electrode (FIG. 4), it is less than the amount of masking where the masker electrode was the $10^{th}$ electrode (FIG. 3).

An SOE curve measured with the subtraction method for a particular probe electrode may be determined by, for example, taking measurements (e.g., ECAPs) for the probe electrode and every possible masker electrode (i.e., all 22 electrodes of electrode array 134). Then, an SOE curve for a different electrode may be determined by setting it as the probe electrode and taking measurements (e.g., ECAPS) of the amount of masking, again from all possible masker electrodes (e.g., all 22 electrodes). A further description of mechanisms for generating SOE functions where the masker and probe electrodes may be different is provided in the above-referenced Cohen et al. 2003 paper and Cohen et al. 2004 paper. Moreover, rather than taking measurements for every possible masker electrode, in other examples for determining an electrophysiological model, the masker electrode may be selected to be every other electrode, every fourth electrode, or may vary in any other appropriate way.

In generating the above-discussed SOE curves, various variables may be used, such as, for example, the probe rate, a masker-to-probe interval (MPI), the number of masking pulses, the rate of the masking pulses, an amplifier gain, the delay of the start of the measurement with respect to the probe pulse, the pulse widths, pulse gaps, or other variables applicable to the NRT™ software. For example, in one embodiment, the MPI interval may be set to +/−400 microseconds and all measurements taken at this MPI. However, in other embodiments, different MPIs may be used, or, for example, a set of measurements may be taken at one MPI value and then other sets of measurements taken at different MPI values. Further, lower MPI's may be used to mimic high stimulation rates. The number of masker pulses and the masker rate may be varied to mimic temporal effects at different stimulation rates. The probe rate is generally kept at a low rate (±50 Hz) to minimize adaptation effects. Likewise, the other variables may also remain fixed for all measurements, may vary, or different sets of measurements may be taken for different values. Additionally, summation effects of masker and probe pulses may be taken into account, such as, for example, when masker-to-pulse intervals are set to values below 300 microseconds.

Further, in the above examples discussing exemplary mechanisms for determining a psychoelectric model, the amplitudes of the stimuli for the masker electrode and the probe electrode may be set to be equal. This current level may be, for example, the Loudest Acceptable Perception Level (LAPL) for the probe electrode, or some value below the LAPL, such, as for example, 80% of the LAPL. Or in other examples, the amplitude for the masker electrode may be set to a value less than the Probe Current Level (PCL) (e.g., 80%, 60%, 40% of the PCL), or even a value greater than the PCL.

Further, in other examples, an SOE curve may be determined for one combination of PCL and masker current level, and then other SOE curves determined for different combinations of PCLs and masker current levels. Also, in other examples, information regarding the psychophysical threshold level and the LAPL for each electrode may be taken into account. For example, if the threshold level for a particular electrode that is being used as the masker electrode has a higher threshold level than other electrodes, a corresponding higher masker current level may be used when this particular electrode is the masker electrode.

Figure 5:
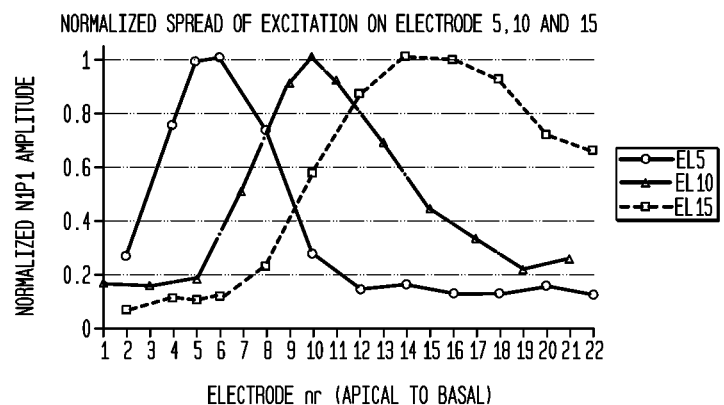
FIG. 5 illustrates exemplary spread of excitation (SOE) curves for an implant recipient where the Masker and Probe Current Levels were set to be equal, in accordance with one embodiment of the present invention.

FIG. 5 illustrates three exemplary spread of excitation (SOE) curves. In this example, a masker-to-probe interval (MPI) of 500 µs was used and the plotted psychoelectric measurements were normalized with respect to the maximum ECAP amplitude. The exemplary SOE curves illustrated in FIG. 5 depict normalized Spread of Excitation measurements carried out on 3 different electrodes (EL5, EL10 and EL15) in a Nucleus® Contour Advance™ recipient. As shown in FIG. 5, the overlap in excitation field may be deduced. For example, EL5 has an excitation field that has overlap with EL2 to EL10, EL10 has an excitation field that has overlap with EL5 to EL16 and EL15 has overlap with EL8 to 22.

Figure 6:
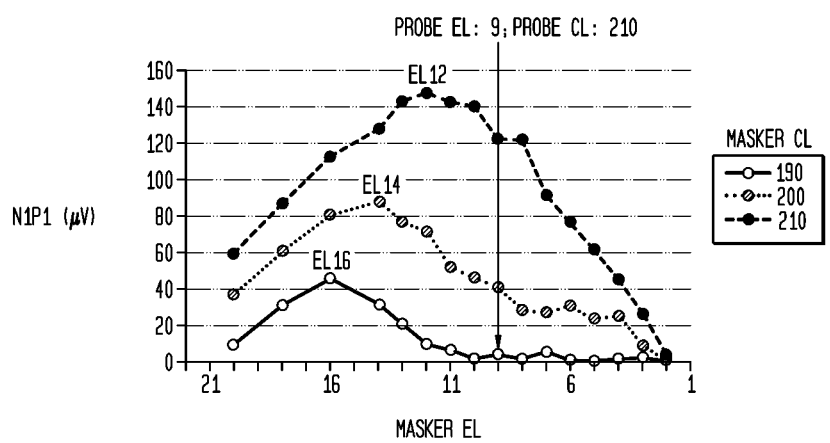
FIG. 6 illustrates another set of exemplary SOE curves for an implant recipient, in accordance with one embodiment of the present invention.

FIG. 6 illustrates another set of exemplary SOE curves for an implant recipient. In this example, the implant recipient was fitted with a C124RE™ cochlear implant, the probe electrode was set as the $9^{th}$ electrode, and the probe current level was set at 210. Further, in this example, measurements were taken for three different masker current levels (190, 200 and 210). As illustrated, in this example, the SOE is not symmetrical around the probe electrode but is greater towards the apical end of the cochlea (i.e., electrode 12 for MCL=210, electrode 14 for MCL=200, and electrode 16 for MCL=190).

Moreover, if the determined SOE curves have a Y-axis that is in terms of microvolts, in an embodiment, this Y-axis is then translated to current levels (CL) for use when taking masking effects into account when determining the stimulation signals to be used, which is described in further detail below. One exemplary method for translating the Y-axis from microvolts to CL includes determining the dynamic range for each electrode; that is, the difference between the psychophysical threshold CL and the maximum comfort level CL for the electrode. Then, the masking thresholds in CL may be determined using the following simplified formula:

Masking Threshold on Electrode $X$=Threshold CL+ ((SOE Amplitude at Electrode $X$)/(SOE Maximum Amplitude))*(Dynamic Range of Electrode $X$)

As one of skill in the art would be aware, the above formula is a simplified formula for explanatory purposes, and that in actual implementations the formula would likely include additional variables.

Figure 7:
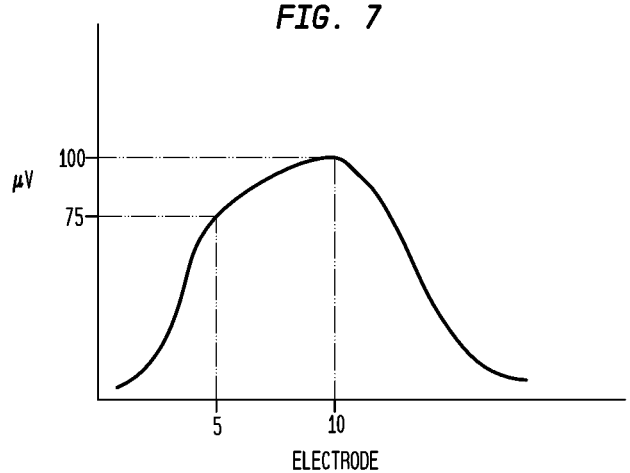
FIG. 7 illustrates an exemplary SOE curve, in accordance with one embodiment of the present invention.

FIG. 7 illustrates an exemplary SOE curve where the masker electrode is electrode 10 and the probe electrode is electrode 5. Further, in this example, electrode 5 has a threshold level of 170 CL and a maximum comfort level of 210 CL (not shown). Thus, the dynamic range for electrode 5 is 40 CL (210 CL–170 CL). As shown, the SOE curve has a maximum amplitude of 100 microvolts. Further, the amplitude of the SOE curve at electrode 5 is 75 microvolts. Thus, using the above calculation, the masking threshold for electrode 5 is equal to [170+((75)/(100)*40)] or 200 CL. This SOE curve may then be completely translated to CLs by, for example, repeating the above calculation for all electrodes on the X-axis (that is, all electrodes of electrode array 134). It should be noted that this is but one example of a method for translating an SOE curve from micro-volts to CLs, and other methods may be used without departing from the scope of the present invention.

For example, instead of using the psychophysical dynamic range of the electrode, one can use the amplitude growth function of the corresponding objective recording method that has been used for the recording of the SOE. The amplitude growth function then defines a transformation from CL to the amplitude of the objective recording in microvolts and vice versa. The threshold level of the response and the LAPL may be used to define the dynamic range and an offset level for a calculation like the one described above.

Further, in one example, once an SOE curve is determined and translated in terms of CLs, it may also be used to generate other SOE curves. Thus, rather than determining SOE curves for all possible combinations of probe electrode and current levels, some SOE curves may be interpolated or extrapolated from other SOE curves. For example, an SOE curve determined by measurements, such as those described above, may be used to generate other SOE curves, such as, for example, for different probe current levels. These interpolated SOE curves may be determined by multiplying all values in the original SOE curve by a particular factor. That is, if the maximum current level for the original SOE curve is 200 CL, it may be translated to an SOE curve with a maximum current level of 180 by multiplying all amplitudes by 9/10 (that is, 180/200). Or in another example, rather than multiplying all amplitudes by a factor, instead a value may be subtracted from all amplitudes. For example, an SOE curve with a maximum amplitude of 200 may be translated to an SOE curve with a maximum amplitude of 180 by subtracting 20 from all the amplitudes.

In addition, to shift SOE curves on the Y-axis (i.e., by amplitudes), these translated curves may also be shifted in the X-axis; that is, shift by electrodes. As with Y-axis shifting, this may also be accomplished by multiplying a factor to the X-axis points (that is, electrodes) or subtracting values from the X-axis points.

Figure 8:
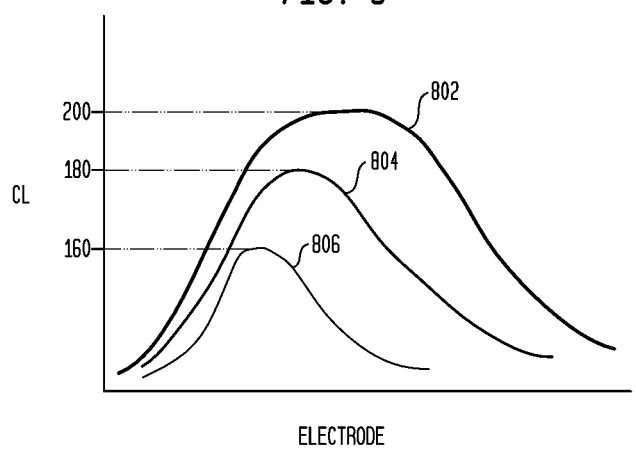
FIG. 8 illustrates a set of exemplary SOE curves exhibiting both Y-axis and X-axis shifting, in accordance with one embodiment of the present invention.

FIG. 8 illustrates a set of exemplary SOE curves exhibiting both Y-axis and X-axis shifting. As illustrated, SOE curve 802 has a maximum current level of 200. This curve may have been determined using a method such as those discussed above. SOE curve 804 may then be generated by translating SOE curve 802 from a maximum current level of 200 to a maximum current level of 180. This may be accomplished by, for example, multiplying the amplitudes of SOE curve 802 by a factor (i.e., 9/10) or by subtracting all amplitudes by a value (i.e., 20). Additionally, the X-axis is also being illustrated as shifting from left to right. This may be accomplished by multiplying or subtracting a value from the X-axis. This value may be based on laboratory measurements indicating an appropriate value for X-axis shifting for this particular implant recipient, or a population of people to which this implant recipient belongs, or the population as a whole. FIG. 8 further illustrates an SOE curve 806 with a maximum current level of 160 that is also generated from translating SOE curve 802 in a like manner. These collections of SOE curves may then be used as the electrophysiological model used for taking masking into account when determining the stimulation signals for stimulating electrode array 134. That is, these SOE curves may be combined with any other SOE curves determined for other electrodes, as described above with reference to block 214 of FIG. 2.

FIG. 6 in the Cohen et al. 2003 paper shows that psycho-electric measured forward masking curves and electro-physiologically measured SOE curves have a clear correlation. This suggests that the use of both masking models would give similar results when used in a compression algorithm. The advantage of the electrophysiological model is that it can be obtained without subjective feedback from the cochlear implant recipient. This is particularly important in young children or psychologically disabled cochlear implant recipients for whom detection of psychophysical masking would not be practicably feasible.

Although the above embodiments for determining an electrophysiological model for a particular implant recipient were discussed with reference to ECAP measurements, in other examples other electrophysiological measurements may be used, such as, for example, electrical auditory brainstem responses (EABRs) or cortically evoked potentials (CEPs).

Figure 9A:
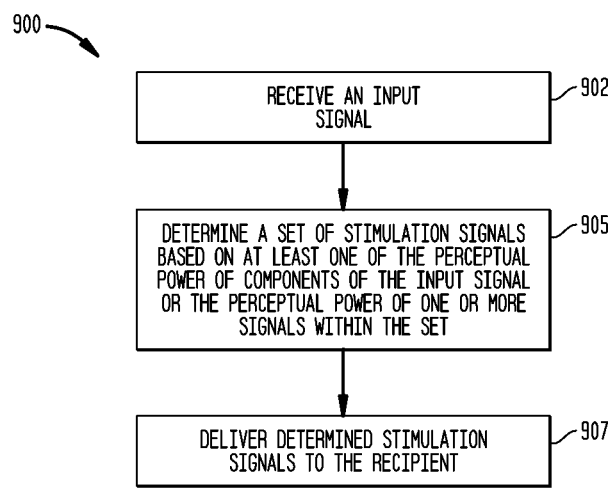
FIG. 9A is a high level flowchart illustrating the operations performed during an exemplary method in accordance with aspects of the present invention.

FIG. 9A is a high level flowchart illustrating the operations performed during an exemplary method in accordance with aspects of the present invention. At block 902, an input signal is received. As noted, the input signal may be received, for example, by microphone 120 and converted to one or more electrical signals. At block 905, a set of stimulation signals is determined based on at least one of the perceptual power of components of the input signal and the perceptual power of one or more signals within the set. For example, as described in greater detail below, in one embodiment the set of stimulation signals is determined based on the frequency components of the input signal. In such embodiments, frequency components of the input signal having the largest perceptual power are converted to stimulation signals and are included in the set. In other embodiments also described in greater detail below, the frequency components of the input signal are converted to stimulation signals, and signals within the set are eliminated or adjusted based on the perceptual power of other signals within the set. This adjustment may be based on the perceptual power of one stimulation signal, the perceptual power of several stimulation signals, the perceptual power of all stimulation signals within the set, or any combination thereof. In either embodiment, at block 907 the determined set of stimulation signals are delivered to the recipient. FIG. 9B illustrates the operations performed during a method in accordance with one embodiment of FIG. 9A. As noted, in certain embodiments an input acoustic signal is received and converted or one or more electrical signals at block 902. A set of stimulation signals are determined at block 905. In accordance with the exemplary embodiments of FIG. 9B, the electrical signals first undergo pre-processing at block 904. This pre-processing may, for example, include using a pre-emphasis filter, automatic gain control (AGC), and/or manual sensitivity control (MSC), such as for example used in the Advanced Combination Encoder (ACE) strategy. This pre-processing may be provided, for example, by microphone 120 or speech processing unit 116. These signals next undergo signal analysis at block 906. As is well known in the art, this may include filtering the signals using a bank of band-pass filters to obtain a plurality of signals. The plurality of obtained signals may each correspond to a channel of cochlear implant 100. For example, in an exemplary cochlear implant 100 having an electrode array 134 which includes 22 electrodes, the signal analysis preferably outputs 22 separate output signals, because each channel of the implant corresponds to one electrode of electrode array 134.

Additionally, in an alternative embodiment, virtual channels may also be generated by, for example, combining the stimulation signals for multiple electrodes, thus resulting in possibly more than 22 output signals. For example, a virtual channel may be for a frequency between the frequencies corresponding to two electrodes of electrode array 134. Then, by appropriately stimulating two or more of the electrodes of electrode array 134, the frequency corresponding to the virtual channel may be perceived by the recipient. For example, intermediate frequencies corresponding to a virtual channel may be achieved by coordinated stimulation of, for example, three electrodes that together cover a frequency band including the desired intermediate frequency. For example, the three electrodes (referred to herein as a triad) may be stimulated at particular amplitudes and according to a particular timing pattern so that the intermediate frequency is perceived by the implant recipient. Or for example, a virtual channel may be used to cause multiple electrodes to be simultaneously stimulated, thus resulting in application of a stimulus to the auditory nerve 138 having a larger spread of excitation (SOE).

These virtual channels may be treated identically to real channels in the presently described embodiments. That is, although the present embodiments are described with reference to a one to one correspondence between electrodes and stimulation channels, in other embodiments, virtual channels may be used and treated in the same manner, for masking purposes, as real channels. For example, rather than simply determining the psychoelectric model in terms of electrodes (i.e., real channels), such as described above with reference to FIGS. 2-8, a psychoelectric model in terms of stimulation channels (i.e., both real and virtual channels) may be determined. In such an example, similar methods to those discussed above may be used for determining the psychoelectric model.

Figure 10:
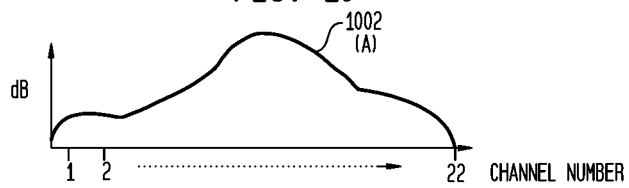
FIG. 10 illustrates an exemplary frequency spectrum of an exemplary received signal, in accordance with one embodiment of the present invention.

In other embodiments, rather than using a plurality of bandpass filters, a Fast Fourier Transform (FFT) may be used to generate the frequency spectrum for the received signal. In such an example, the FFT may, for example, compute 22 spectrum amplitudes (one for each channel) between 125 and 8 kHz. Further, as discussed above, virtual channels may be employed allowing for the number of channels to be greater than the number of electrodes. After signal analysis, the resulting signals may then be equalized at block 908. FIG. 10 illustrates an exemplary frequency spectrum 1002 of an exemplary received signal after equalization.

Stimulation signals to be delivered to the recipient are then determined. The following provides a more detailed description of one exemplary method for determining stimulation signals. This exemplary method may, for example, be performed by the speech processing unit 116 of cochlear prosthesis 100. Or in other examples, the following method may be performed by other hardware or software, or any combination thereof. Moreover, the following provides one exemplary method, and other methods may be used without departing from the invention.

Figure 11:
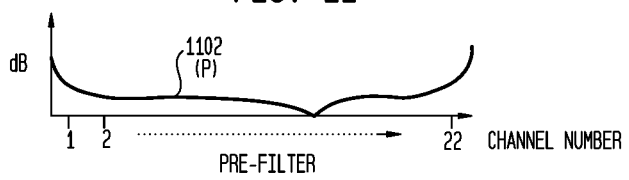
FIG. 11 illustrates an exemplary frequency spectrum of a pre-filter for pre-processing of the signal, in accordance with one embodiment of the present invention.

First, a frequency spectrum for pre-filtering the equalized signal is applied at block 916. FIG. 11 illustrates an exemplary frequency spectrum 1102 of a pre-filter that may be used for pre-processing of the signal. Such a pre-filtering step would only be necessary when a pre-emphasis filter is not applied during the pre-processing step of block 904. As illustrated, this exemplary pre-filter approximates an equal loudness function. A further explanation of such an exemplary pre-filter is provided in the above-referenced Baumgarte reference. For example, the pre-filter may be used to compensate for varying thresholds-in-quiet at different frequencies (e.g., the electrodes corresponding to the frequencies). A threshold in quiet is used to compensate for the fact that a normal hearing person does not perceive every frequency with the same intensity. The pre-filter may then, for example, be an equal loudness function that compensates for these varying thresholds in quiet. This pre-filter is used to identify the signal components which have the highest perceptual power and, as described below, to permit selection of maxima based on perceptual, rather than spectral power.

Figure 12:
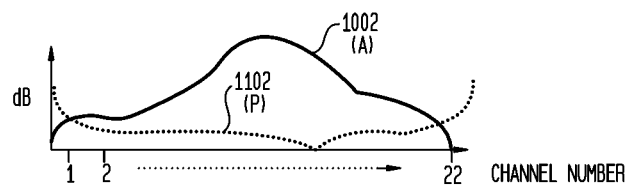
FIG. 12 further illustrates the combination of the frequency spectrum of the exemplary received signal and the frequency spectrum of a pre-filter, in accordance with one embodiment of the present invention.
Figure 13:
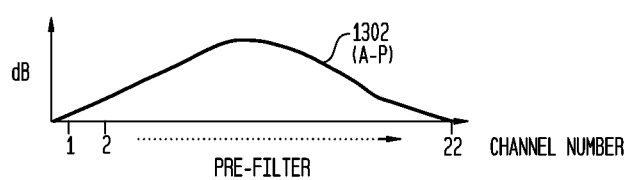
FIG. 13 illustrates the total masking effect resulting from the frequency spectrum illustrated in FIG. 12.
Figure 14:
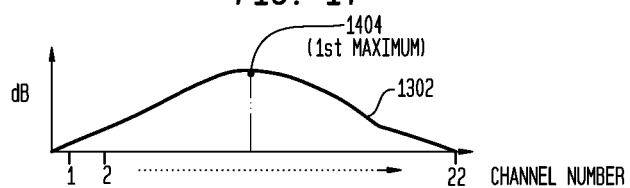
FIG. 14 illustrates a frequency spectrum along with a determined maxima, in accordance with one embodiment of the present invention.

Next, the computed frequency spectrum is applied to the received signal block 918. FIG. 12 further illustrates the combination of the frequency spectrum 1002 (FIG. 10) of the exemplary received signal and the frequency spectrum 1102 (FIG. 11) of the pre-filter and FIG. 13 illustrates the resulting frequency spectrum 1302 (i.e. frequency spectrum 1002 minus frequency spectrum 1102). After application of the computed spectrum to the received signal, the maxima (that is, the channel having the largest perceptual power) for the resulting spectrum is determined at block 920. FIG. 14 illustrates resulting frequency spectrum 1302 along with the determined maxima 1404.

After the maxima is determined, the masking effect that would be caused by the selected maxima is determined and this masking effect is combined with the frequency spectrum 1102 of the pre-filter at block 922. In this embodiment, the masking effect of the selected maxima is determined using one of the above-discussed models. For example, a psychoelectric model determined for this user may be used. In other embodiments, rather than using a psychoelectric model generated for this particular implant recipient, a psychoelectric model for a particular group of people may be used. For example, if for some reason it is not possible or desirable to measure the masking effect for the implant recipient, the system may instead use a psychoelectric model for a group of people (e.g., implant recipients) sharing a common characteristic with the implant recipient (e.g., age, gender, etc.). Or, for example, the system may use a psychoacoustic model, such as, for example, a generic psychoacoustic model for the population as a whole, such as, for example, the MPEG1 Psychoacoustic Model 1 or Model 2. Or, the system may use a psychoacoustic model for a particular group of people (e.g., people with normal hearing) sharing a common characteristic with the implant recipient (e.g., age, gender, etc.). Additionally, the masking model utilized may be in terms of dBSPL, CL, or microvolts, and as discussed above these models may be translated into one another. In this example, the selected model is translated into a model in terms of CLs and electrodes (if necessary), and this model is used in determining the masking effects for the selected maxima. The combination of the masking effect and the pre-filter will be referred to as the total masking effect.

Figure 15:
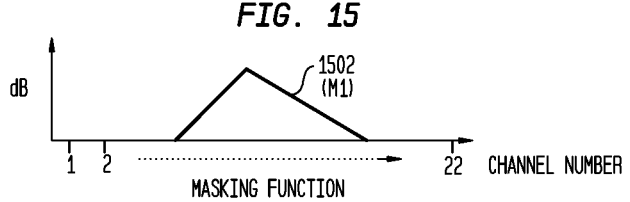
FIG. 15 illustrates an exemplary frequency spectrum of the masking effect for a selected maxima, in accordance with one embodiment of the present invention.
Figure 16:
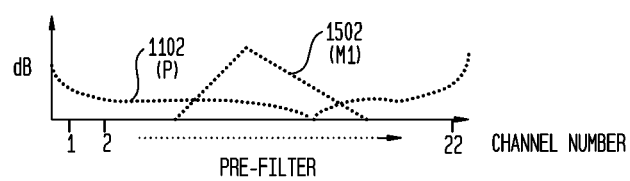
FIG. 16 illustrates an exemplary frequency spectrum of the masking effect for a selected maxima along with the frequency spectrum of a pre-filter, in accordance with one embodiment of the present invention.
Figure 17:
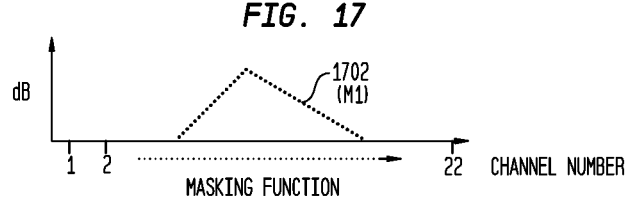
FIG. 17 illustrates a resulting total masking effect, in accordance with one embodiment of the present invention.

FIG. 15 illustrates the exemplary frequency spectrum 1502 of the masking effect for the selected maxima 1404. That is, FIG. 15 is a curve that indicates for each frequency the amount of masking as attenuation in dB. FIG. 16 illustrates the exemplary frequency spectrum 1502 of the masking effect for the selected maxima 1404 along with the frequency spectrum 1102 of the pre-filter. FIG. 17 illustrates the resulting total masking effect spectrum 1702. The total masking effect is the sum of the masking effects of all selected channels. Because only one channel has been selected, the total masking effect 1702 is equivalent to masking effect 1502 of the selected channel.

Next, it is determined whether the desired number of channels has been selected at block 924. For example, in one embodiment it may be desirable to determine 8 maxima for stimulation of electrode array 134. Thus, in this example, the process will continue until all 8 maxima are determined or until the total masking effect indicated that no other maxima needs to be determined (for example, the difference between the frequency spectrum of the received signal and the combined frequency spectrum of the masking effects is equal or smaller than a predefined threshold). In an alternative embodiment, a dynamic number of maxima are determined based on the amount of information in the signal. For example, if there is a large broad peak, there is a single maxima, while if there are multiple narrower peaks more maxima will be stimulated. In other words, in this embodiment, the number of maxima dynamically depends on the spectral shapes and amount of masking. It should be appreciated that it is possible to adjust the stimulus artifact to make a loudness correction based on a loudness model.

Figure 18:
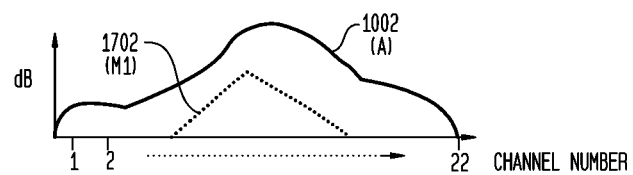
FIG. 18 illustrates the exemplary frequency spectrum of a total masking effect and the frequency spectrum of a received signal, in accordance with one embodiment of the present invention.
Figure 19:
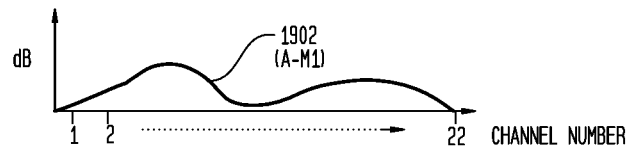
FIG. 19 illustrates a resulting frequency spectrum, in accordance with one embodiment of the present invention.
Figure 20:
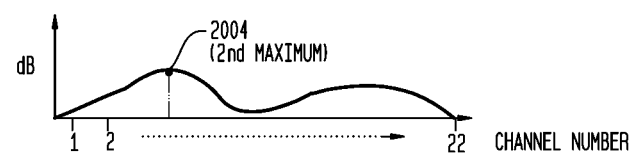
FIG. 20 illustrates a frequency spectrum along with a determined maxima, in accordance with one embodiment of the present invention.

If more maxima should be determined, the process returns to block 918 and the total masking effect is applied to the received signal (in this particular example it is subtracted) at block 922. FIG. 18 illustrates both the exemplary frequency spectrum 1702 of the total masking effect and the frequency spectrum 1002 of the received signal. FIG. 19 illustrates the resulting frequency spectrum 1902 (i.e. frequency spectrum 1002 minus frequency spectrum 1702). The next maxima is then determined at block 920. FIG. 20 illustrates frequency spectrum 1902 along with determined maxima 2004. Next, the masking effect of this next maxima is determined and is combined with the masking effects of the prior selected maxima and the pre-filter at block 922.

If more maxima should be determined at block 924, the process again returns to block 918 and the combined total masking effect is then subtracted from the frequency spectrum 1002 of the received signal and another maxima determined. This process may then repeat until all desired maxima are determined.

Figure 21:
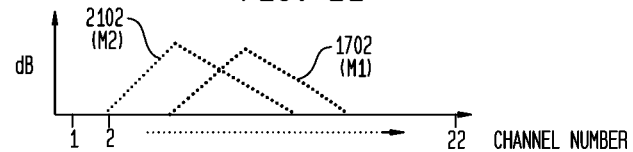
FIG. 21 illustrates a frequency spectrum of a new masker along with a prior determined total masking effect, in accordance with one embodiment of the present invention.
Figure 22:
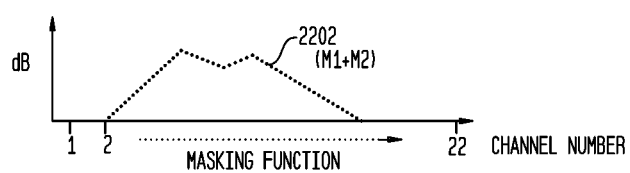
FIG. 22 illustrates a total masking effect frequency spectrum, in accordance with one embodiment of the present invention.
Figure 23:
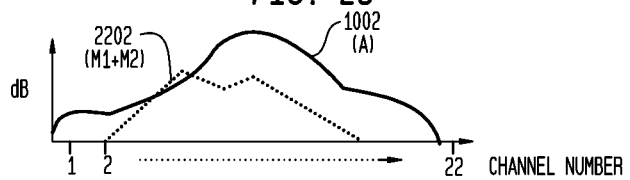
FIG. 23 illustrates a total masking effect frequency spectrum 2102 and a frequency spectrum of a received signal, in accordance with one embodiment of the present invention.
Figure 24:
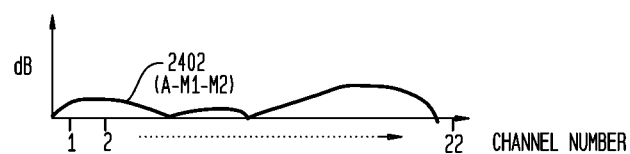
FIG. 24 illustrates a resulting frequency spectrum, in accordance with one embodiment of the present invention.

FIG. 21 illustrates the frequency spectrum 2102 of this new masker along with the prior determined total masking effect 1702. These combine to create the total masking effect frequency spectrum 2202 illustrated in FIG. 22. Although the total masking effect is additive here, the total masking effect 2202 may be non-linear or something other than the sum. This total masking effect spectrum 2202 is then subtracted from the frequency spectrum of the received signal 1002 as illustrated in FIG. 23. This results in frequency spectrum 2402 illustrated in FIG. 24. The maxima for this resulting spectrum may then be determined and the process repeated, for example, until all maxima are determined or no other maxima can be determined.

After determination of the stimulation signals, a loudness growth function may be used on the determined stimulation signals at block 912. After which, the signals may be sent to electrode array 134 for stimulating auditory nerve 138 at block 914. As discussed above, these stimulation signals may be real channels (i.e., corresponding to a single electrode) and/or virtual channels involving, for example, the simultaneous or coordinated stimulation of multiple electrodes.

Figure 9C:
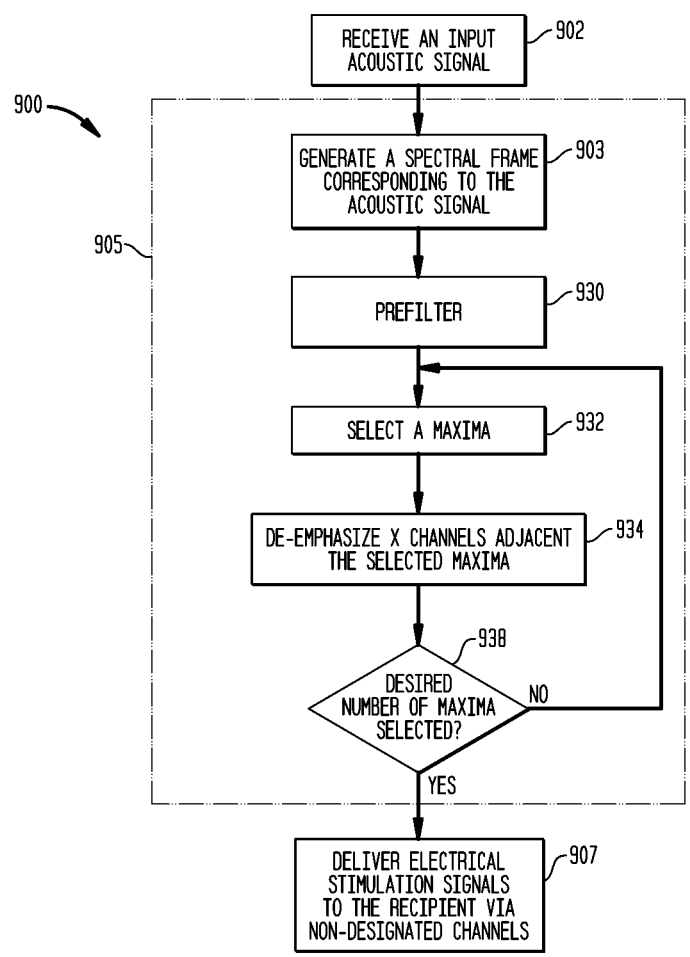
FIG. 9C is detail level flowchart illustrating the operations performed during a method in accordance with one embodiment of FIG. 9A.

FIG. 9C illustrates the operations performed during a method in accordance with embodiments of FIG. 9A. In these embodiments, the perceptual significance of components of an input signal are used to determine which channels should be used to deliver a set of stimulation signals to the recipient. This is sometimes referred to herein as an N of M strategy.

Specifically, a set of stimulation signals is determined based on the perceptual power of an input signal. Frequency components of the input signal having the highest perceptual power are included within the set of stimulation signals for delivery via selected channels of the tissue-stimulating device. Signals delivered via channels adjacent the selected channels are designated as likely to be masked by the stimulation signals within the set. As such, frequency components corresponding to these adjacent channels are not included within the stimulation set. The determined set of stimulation signals are then delivered to the recipient.

In the illustrative embodiment of FIG. 9C, an input acoustic signal is received and converted to one or more electrical signals at block 902. A set of stimulation signals are determined at block 905 using, for example, the following method. The electrical signals first undergo processing at block 903 in order to generate a spectral frame corresponding to the received acoustic signal. The operations of block 903 includes pre-processing and signal analysis as described above with reference to FIG. 9B so as to obtain a plurality of signals. This processing may be done using a plurality of band-pass filters, FFT, etc. The spectral frame is a vector that represents the spectral power per channel of the filter-bank obtained during the pre-processing and signal analysis stages.

Following the above processing, frequency spectrum for pre-filtering the components of the input signal is applied at block 930. As illustrated, this exemplary pre-filter approximates an equal loudness function. A further explanation of such an exemplary pre-filter is provided in the above-referenced Baumgarte reference. For example, the pre-filter may be used to compensate for varying thresholds-in-quiet at different frequencies. As would be appreciated, the pre-filtering step of block 930 would be unnecessary in embodiments which use a directional microphone with appropriate frequency response, a pre-emphasis filter applied during the pre-processing step of block 903, or when a pre-emphasized input is used.

In these embodiments, using the information derived from application of the threshold in quiet pre-filter, the signal component having the highest perceptual power is selected at block 932. This signal component is referred to herein as a selected maxima. Upon selection of the maxima, the method automatically determines that X channels near or adjacent the selected channel will likely be masked upon delivery of stimulation in accordance with the selected maxima. That is, due to the perceptual power of the selected signal component, signals delivered via the X channels will likely not be perceived by the recipient. As such, at block 934, X channels adjacent the selected maxima are designated as unfavorable channels for delivery of a stimulation signal. In other words, these adjacent channels are deemphasized such that that will likely not be chosen for delivery of stimulation signals. As would be appreciated, the number of deemphasized channels X may be asymmetric around the selected maxima.

At block 938, a determination is made as to whether all maxima have been selected and the resulting masking information determined. If all maxima have not been selected, the method returns to block 932 for selection of the next maxima. The next selected maxima may comprise, for example, the maxima having the next highest perceptual power. The above process continues until a desired number maxima have been selected and the corresponding masking effect determined. For example, in certain embodiments, 8 maxima may be selected and the corresponding masking effect determined.

Once the desired number of maxima have been selected, the method proceeds to block 907 where stimulation signals are generated for delivery to the recipient. The stimulation signals are only delivered via channels which have not been de-emphasized.

Figure 9D:
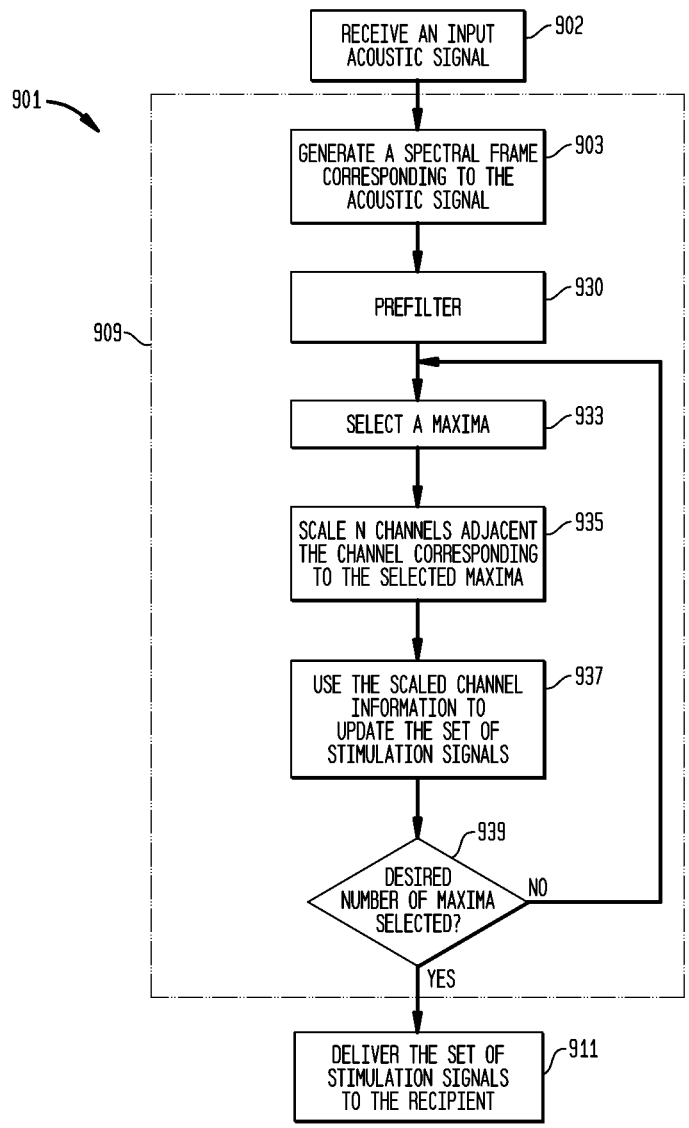
FIG. 9D is detail level flowchart illustrating the operations performed during a method in accordance with one embodiment of FIG. 9A.

FIG. 9D illustrates the operations performed during a method in accordance with other embodiments of FIG. 9A. The embodiments illustrated in FIG. 9D may involve application of a simple masking scheme in which certain stimulation signals are automatically deemed masked and adjusted accordingly.

At block 902, an input acoustic signal is received. A set of stimulation signals are determined at block 905 using, for example, the following method. The electrical signals first undergo processing at block 903 in order to generate a spectral frame corresponding to the received acoustic signal. The operations of block 903 includes pre-processing and signal analysis as described above with reference to FIG. 9B so as to obtain a plurality of signals. This processing may be done using a plurality of band-pass filters, FFT, etc. The spectral frame is a vector that represents the spectral power per channel of the filter-bank obtained during the pre-processing and signal analysis stages. Following the above processing, frequency spectrum for pre-filtering the components of the input signal is applied at block 930. As illustrated, this exemplary pre-filter approximates an equal loudness function. A further explanation of such an exemplary pre-filter is provided in the above-referenced Baumgarte reference. For example, the pre-filter may be used to compensate for varying thresholds-in-quiet at different frequencies. As would be appreciated, the pre-filtering step of block 930 would be unnecessary in embodiments which use a directional microphone with appropriate frequency response, a pre-emphasis filter applied during the pre-processing step of block 903, or when a pre-emphasized input is used.

A first stimulation signal having the largest perceptual power is then selected at block 933. This signal is referred to herein as a selected maxima. As noted, this selected maxima is configured to be used to generate stimulation configured to be delivered via a selected channel of the cochlear implant. Upon selection of the maxima, the method automatically determines that X channels near or adjacent the selected channel will likely be masked upon delivery of stimulation in accordance with the selected maxima. That is, due to the perceptual power of the selected signal, signals delivered via the X channels will likely not be perceived by the recipient. As such, at block 935, the amplitudes of any stimulation signals corresponding to these X channels are scaled to account for this likely masking.

As would be appreciated, the scaling may be applied to the signal as a simple multiplication, a subtraction or a more complex function derived from the scaling factor S as would be apparent to one skilled in the art. As described below in more detail, the number of channels X and the scaling S applied to the stimulation signals are configurable. The selection and determination of the number of channels and the applied scaling are described below with reference to FIGS. 26-28.

In some embodiments, the stimulation signals delivered via the X channels are scaled so as to increase the amplitudes. The increased amplitude allows the stimulation corresponding to the signal to be perceived by the recipient. In certain embodiments, the stimulation signals are scaled so as to eliminate stimulation on the X channels.

At block 937, the processed and analyzed stimulation signals are updated using the selected maxima and scaled channel information. At block 939, a determination is made as to whether a desired number of maxima have been selected and the resulting masking information determined. If the desired number of maxima have not been selected, the method returns to block 933 for selection of the next maxima. The next selected maxima may comprise, for example, the maxima having the next highest perceptual power. The above process continues until all desired maxima have been selected and the corresponding masking effect used to adjust the set of stimulation signals.

Once all maxima have been selected and the stimulation set is adjusted to account for the corresponding masking effects, the method proceeds to block 911 where the determined set of stimulation signals are delivered to the recipient.

As noted, the amplitudes of the signals corresponding to the X channels may be scaled to account for this likely masking effect. This scaling may increase or decrease the corresponding stimulation delivered to the recipient. It may also be applied temporarily to weight the subsequent selection of channels.

As noted above, the number of channels X is configurable. For example, in certain embodiments, 1, 2, 3, etc. channels on either side of the selected channel may be automatically deemed masked and scaled accordingly. In other embodiments, a single channel on one side of the selected channel may be scaled. Alternatively, the number of channels influenced by the selected maxima may be asymmetric about the selected maxima. In yet another embodiment the number of channels that are likely to be scaled on either side of the selected channel may be different for each channel. For example, the spread of likely masking may be wider for a low frequency channel compared to a high frequency channel.

Figure 9E:
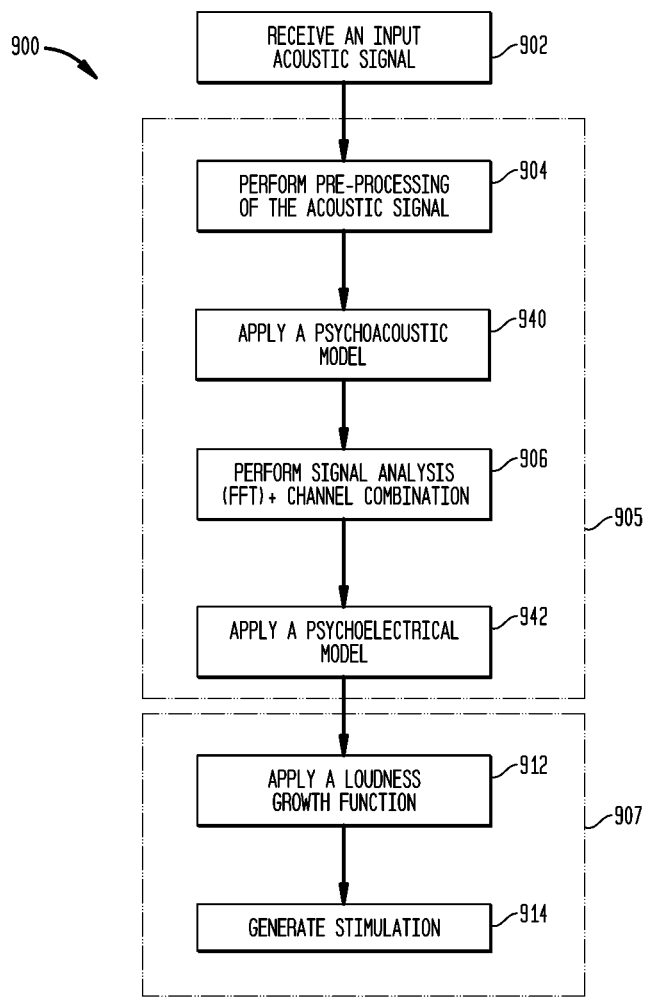
FIG. 9E is detail level flowchart illustrating the operations performed during a method in accordance with one embodiment of FIG. 9A.

FIG. 9E illustrates the operations performed during a method in accordance with another embodiment of FIG. 9A. In this illustrative embodiment of the present invention, both a psychoacoustic model and a psychoelectric model may be used to determine likely masked signals. For example, a psychoacoustic model may be applied first to exclude stimulation pulses that are redundant to a normal hearing person because they are masked. Then, a psychoelectric model (e.g., a user specific model) may be used to remove stimulation pulses that are redundant to the implant user because they will be masked (i.e., the signal would be masked by another larger amplitude signal). This scheme would lead to a power saving (less stimulation) without loss of performance. Or, alternatively, a psychoelectric model may be used to determine what signals would be masked, and then boost their amplitude to compensate for the electrical masking that is not present in normal hearing. This may lead to improved perception of the sound. This permits signals that would be heard by a normal hearing person, but masked for an implant recipient, to be perceived by the implant recipient.

At block 902, microphone 120 receives sounds which are converted to electrical signals. These signals may then undergo pre-processing at block 904. This pre-processing, as with some of the above-discussed embodiments, may include using a pre-emphasis filter, automatic gain control (AGC), and/or manual sensitivity control (MSC), such as, for example, that used in the Advanced Combination Encoder (ACE) strategy.

Next, the signal undergoes a masking check using a psychoacoustic model at block 940. The model is used to determine which components of the signal processed signal are likely psychoacoustically masked. Components which are likely masked may be removed. This model may, for example, be the MPEG1 Psychoacoustic Model 1, the MPEG1 Psychoacoustic Model 2, or, for example, any other psychoacoustic model now or later developed. Further, for example, the same or a similar strategy for applying the psychoacoustic model may be used as is commonly used in the MPEG Audio Layer-3 format (commonly referred to as MP3).

After performing the psychoacoustic masking, the resulting signal then undergoes signal analysis at block 906. For example, as discussed above with reference to block 906 of FIG. 9A, this may include filtering the signals using a bank of band-pass filters to obtain a plurality of signals as is well-know to those of ordinary skill in the art. Moreover, in a cochlear prosthesis 100 where electrode array 134 includes 22 electrodes, the signal analysis may output 22 separate output signals, one corresponding to each electrode of electrode array 134. Additionally, in other embodiments, as discussed above, virtual channels may also be generated, thus resulting in possibly more than 22 output channels. Because, in this example, the psychoacoustic masking is applied prior to performing the signal analysis of block 906, this method is referred to as a method employing forward processing of the psychoacoustic masking. The psychoacoustic masking of block 940 may be determined in speech processing unit 116 of cochlear prosthesis 100.

The signal undergoes a masking check using a psychoelectric model at block 942. The operations implemented to perform this step may be, for example, similar to the operations performed in connection with block 905 discussed above with reference to FIG. 9B.

In an alternative embodiment, a psychoelectric model may be used to generate a masking table. The table is used to determine which stimulation signals within a given stimulation set are likely masked. The psychoelectric model used in such embodiments may, for example, be a user-specific model determined using a method for determining a user-specific psychoelectric model, such as, for example, the above-described method of FIG. 2. Alternatively, the psychoelectric model may be a model for all cochlear prosthesis recipients or a subset of recipients for which the recipient is a member.

In another exemplary embodiment of the present invention, rather than deleting signals that otherwise would be electrically masked for an implant recipient, the intensity of these signals may be increased so that they are perceived by the recipient. For example, application of the psychoacoustic model at block 940 provides the frequencies that would be perceived by a normal hearing person. Some of these frequencies, however, may otherwise be masked in an implant due to stimulation of other electrodes of electrode array 134. Thus, in this embodiment, rather than deleting these signals that would otherwise be masked in an implant recipient, the signals are instead increased so that they are perceived by the implant recipient. In certain such embodiments, the required intensity for perception may also be determined. For example, in a normal hearing person, the frequency that otherwise would be masked would be perceived in a normal hearing person at a certain intensity level. This information, in conjunction with the masking information may be used to determine the intensity level for the signal so that it is perceived by the implant recipient at an intensity level approximating the intensity level for which a normal hearing individual would perceive the frequency.

Returning to the exemplary embodiments of FIG. 9E, after determination of the set of stimulation signals through application of the various models, a loudness growth function may be applied to the signals at block 912 and the stimulation signals may be sent to electrode array 134 for stimulating auditory nerve 138 at block 914, such as was discussed above. As discussed above, these stimulation signals selected for stimulating auditory nerve 138 may be real channels (i.e., corresponding to a single electrode) and/or virtual channels involving, for example, the simultaneous or coordinated stimulation of multiple electrodes. Further, as with the above embodiments, one or more of the above steps may be performed by speech processing unit 116 of cochlear prosthesis 100.

FIG. 9F illustrates the operations performed during a method in accordance with another embodiment of FIG. 9A. Specifically, FIG. 9F illustrates one embodiment in which both a psychoacoustic model and a psychoelectric model are used to determine a set of stimulation signals. This exemplary method is substantially similar to the above-discussed method of FIG. 9E with the exception that in this example the psychoacoustic model is applied after signal analysis (e.g., splitting the received signal into a plurality of stimulation signals corresponding to one or more of the electrodes of electrode array 134). Because in this example the psychoacoustic model is applied after signal analysis block 906, this method is referred to as a process employing backend processing of the psychoacoustic model. Further, in this example, the psychoacoustic model applied at block 940, as with the above-discussed embodiments, may be a model such as the MPEG1 Psychoacoustic Model 1 or Model 2, or may be a model for a group of people sharing a common characteristic with the implant recipient. Moreover, in this example, the psychoacoustic model may be applied using a method such as is commonly used for applying psychoacoustic models, such as the methodology employed by the MP3 format; or, for example a method such as the above discussed method.

In other exemplary embodiments of the present invention, a masking table is created for the implant recipient, or, in other embodiments, a generic masking table may be used that applies, for example, to the population as a whole or to a particular subset of the population to which the implant recipient shares a common characteristic. Additionally, this masking table may be based on psychophysical measurements including psychoelectric or electrophysiological measurements.

The masking table may, for example, include a set of minimum masked threshold level for each electrode of electrode array 134. For each electrode there is a list of masking levels for the other electrodes, that if the particular electrode is stimulated, the other electrodes will not be stimulated unless their amplitude is above their masking level. For each electrode these unmasking levels can be specified in absolute CLs or relative percentages to the stimulation of the original electrode. An exemplary masking table is listed below for one electrode, n.

As shown, the masking table may include a column identifying each electrode of electrode array 134 along with corresponding minimum unmasked levels. Each unmasked level may, for example, give the minimum stimulus level (e.g., minimum current level) to electrode n which will elicit a response immediately following a stimulus to one or more relevant electrodes. In a complete masking model all electrodes of the array could be considered as relevant. Further, these minimum levels may be expressed as values between the psychophysical threshold (T) and psychophysical maximum comfort (C) levels of the corresponding electrode. The threshold (T) and maximum comfort (C) levels may be determined during the fitting of cochlear prosthesis 100.

| MINIMUM UNMASKED LEVELS | |
| --- | --- |
| Electrode | Minimum Unmasked Levels |
| 1 | $M_{1,T}, M_{1,T+1}, \ldots M_{1,C-1}, M_{1,C}$ |
| 2 | $M_{2,T}, M_{2,T+1}, \ldots M_{2,C-1}, M_{2,C}$ |
| ... | ... |
| n − 1 | $M_{n-1,T}, M_{n-1,T+1}, \ldots M_{n-1,C-1}, M_{n-1,C}$ |
| n + 1 | $M_{n+1,T}, M_{n+1,T+1}, \ldots M_{n+1,C-1}, M_{n+1,C}$ |
| ... | ... |
| ... | ... |

It should be understood this is but one example of a masking table and other types of masking tables may be used without departing from the invention. This determined table may then be used in implementing a masking scheme to delete or replace signals.

The above methods described above with reference to FIGS. 9B-9E provide several examples of methods for taking masking effects into account when determining stimulation signals for use in a cochlear prosthesis 100. Other methods of course can be used without departing from the invention. Moreover, as would be apparent to one of skill in the art, the above described steps and methods may be interchanged, combined, or replaced with other steps without departing from the invention, which is defined in the below claims.

Figure 25:
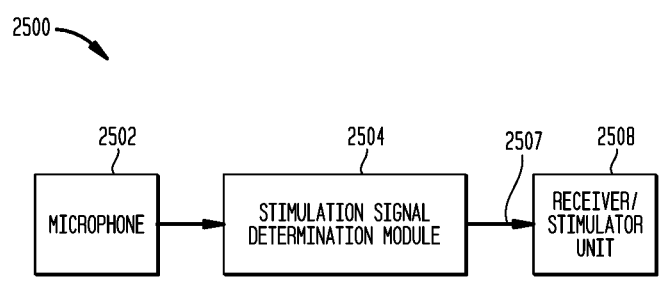
FIG. 25 is a functional block diagram of components of a cochlear implant in accordance with embodiments of the present invention.

FIG. 25 is a functional block diagram illustrating components of a cochlear implant 100 in accordance with embodiments of the present invention. As shown, cochlear implant 100 includes a sound input element, such as microphone 2502 which receives input signals. These signals are converted to a set of stimulation signals for delivery to a recipient by stimulation signal determination module 2505. Specifically, at module 2505, the input signal is processed into a predetermined number of frequency channels. Module 2505 generates a set of signal amplitudes per channel and selects certain channels as the basis for stimulation. These steps may also include, for example, the processing and equalization discussed above with reference to FIGS. 9A-9E. These steps may occur in speech processing unit 116 or, for example, in other hardware or software or any combination thereof.

In the context of the present invention, the signal determination and/or channel selection step carried out by module 2504 would also take into account the effect of masking (based on one or more of the aforementioned models FIGS. 9A-9E). Through the consideration of masking certain channels may be removed from the stimulation set, or the level at which a channels is presented may be altered.

As noted, the scaling factors S used to scale the stimulation signals corresponding to the X channels may also be configurable. In certain embodiments, all stimulation signals within X channels of the selected channel may be scaled by the same scaling factor S. In other embodiments, different scaling factors S may be applied to each of the channels to be scaled. For example, in an embodiment in which X=2, two channels to the left, and 2 channels to the right of the selected channel would be deemed masked and thus scaled accordingly. In such embodiments, a first scaling factor S could be applied to channels directly adjacent the selected channel and a different scaling factor S could be applied to the second set of channels farther away from the selected channel.

As would be appreciated, in embodiments of the present invention, as the definition of masking spread distances X, and scaling factors S become increasingly complex and numerous, the control and configuration of these parameters becomes increasingly difficult. As such, embodiments of the present invention are directed to providing a method in which the parameters X and S may be coupled so that these parameters may be tuned globally for a recipient. In the exemplary embodiment described below with reference to FIG. 26, four parameters, $X_A$ (number of likely masked apical channels), $X_B$ (number of likely masked basilar channels), $S_A$ (scaling factor applied to $X_A$ channels) and $S_B$ (scaling factor applied to $X_B$ channels) are coupled so as to provide global tuning. Apical channels refer to channels that are closer to the cochlea apex than the selected channel. Basilar channels refer to channels that are closer to the entry point of the electrode array into the cochlea than the selected channel.

Although embodiments of the present invention are primarily discussed herein with reference to $X_A$, $X_B$, $S_A$ and $S_B$, the number of channels to be scaled X and/or scaling factors S may be increased or decreased without departing from the scope of the present invention.

Figure 26:
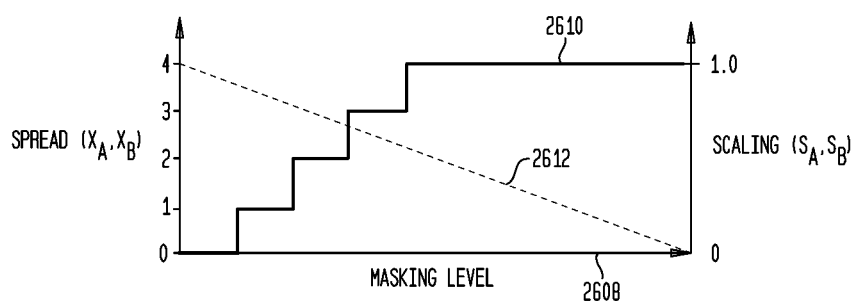
FIG. 26 is a schematic diagram illustrating the coupling of masking parameters in accordance with embodiments of the present invention.

In the embodiments illustrated in FIG. 26, the four masking parameters ($X_A$, $X_B$, $S_A$, and $S_B$) are coupled to a single parameter that describes the amount of masking provided by a selected stimulation signal. This parameter is referred herein to as the masking level. As shown in FIG. 26, as masking level 2608 increases, the spread ($X_A$ and $X_B$), illustrated as line 2610, also increase. However, as the masking level increases, the scalers ($S_A$ and $S_B$), illustrated as line 2612, decrease. At the lower limit of masking level 2608, spread 2610 is zero and scaling factors 2612 are one. In contrast, at the upper limit of masking level 2608, the scaler is set to approximately zero, effectively removing those channels from the selection process. As would be appreciated, other methods for coupling X and S may be used and are within the scope of the present invention.

In accordance with certain embodiments the masking parameters discussed above may be adjusted automatically. In these embodiments, when a signal is received by the cochlear implant, information from the received signal is obtained and this information is used to adjust the masking parameters which will be used when the determining a set of stimulation signals as discussed above. Such embodiments may increase or decrease the effect of masking based on the obtained information. For example, in one such embodiment, information obtained from the input signal may indicate that the recipient is attempting to listen to a speech signal in the presence of a competing background noise. In this case the amount of masking may be increased to ensure that only the strongest signal components are selected, those of the speaker. In contrast if the system detects the recipient is in a quiet environment the system may deem the need for masking to be low and the amount of masking consequently is automatically decreased.

As noted above, upon selection of a maxima, X channels near the channel corresponding to the selected maxima, referred to as the selected channel, are automatically deemed masked. The amplitudes of stimulation signals which are configured to be delivered via these X channels may then each be adjusted to account for the likely masking. For example, the amplitudes of these signals may be scaled by, for example, multiplying, adding, or subtracting a scaling factor S from the amplitude.

In embodiments of the present invention, the number of channels X and the scaling factors S are automatically determined when a maxima is selected based on masking estimations. The amplitudes of signals within the stimulation set (i.e. those on any of the X channels) are then adjusted according to these parameters. In such embodiments, the parameters X and S would be pre-determined. Various methods for determining the parameters X and S are described below with reference to FIGS. 27 and 28.

In embodiments of the present invention, the number of channels $X_A$ and $X_B$ are set to default values for each channel, and the scaling factors $S_A$ and $S_B$ may be determined for the recipient. For example, in some embodiments, it is known that delivery via a channel may result in the masking of one channel on one side of the selected channel, and the masking of two channels on the other side of the selected channel. In specific such embodiments, one basilar channel (i.e. a channel that is located closer to the entry of the electrode array into the cochlea than the selected channel) and two apical channels (i.e. channels closer to the cochlea apex than the selected channel) would be deemed automatically masked. In these embodiments of the present invention, one or more algorithms may then be used to determine $S_A$ and $S_B$, for one or more channels of the recipient. For example, two algorithms may be provided and the output of these algorithms may be matched using a variety of input signals to determine $S_A$ and $S_B$.

In some embodiments, $S_A$ and $S_B$ may be set to the same value for a channel of the cochlear implant. In other embodiments, $S_A$ and $S_B$ may be set to different values for a channel. Also, in certain embodiments, $S_A$ and $S_B$ may be the same across all channels of the implant, or $S_A$ and $S_B$ may vary depending on the channel.

Figure 27:
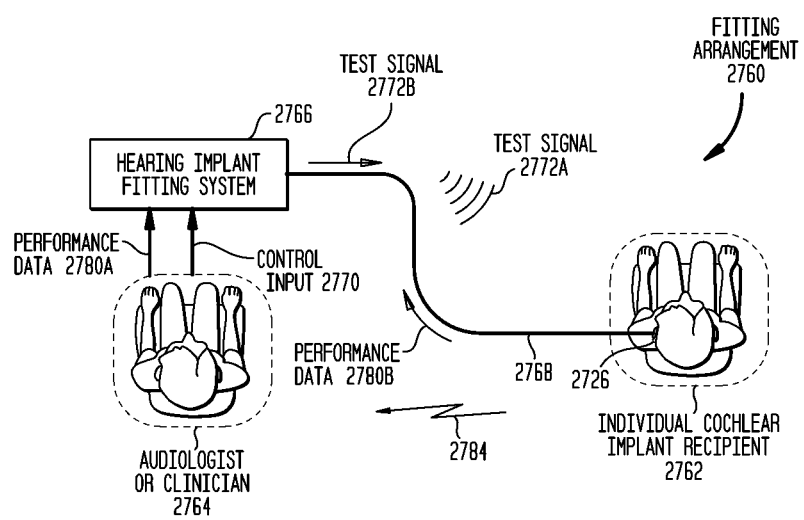
FIG. 27 is a schematic diagram illustrating one exemplary fitting arrangement for use in determining masking parameters in accordance with one embodiment of the present invention.

In further embodiments of the present invention, the number of channels $X_A$ and $X_B$, and/or scaling factors $S_A$ and $S_B$ may be tuned for the recipient. In such embodiments, $X_A$, $X_B$, $S_A$, and $S_B$ would be set to default values, and these values would be customized for the recipient during a fitting procedure. FIG. 27 illustrates an exemplary fitting arrangement 2760 in which a fitting procedure in accordance with embodiments of the present invention may be implemented.

As shown in FIG. 27, an audiologist or clinician 2764 uses a hearing implant fitting system 2766 to deliver signals 2772 to a recipient 2762. These test signals may be an electrical signal 2772B delivered by a cable 2768, or may be presented by free field transmission. Based on the recipient's subjective or objective response to the test signal 2772, clinician 2764 determines the number of channels ($X_A$ and $X_B$) and/or scaling factors ($S_A$ and $S_B$) that provide optimal speech understanding and comfort for recipient 2762. This optimization may be performed for any number of the masking parameters ($X_A$, $X_B$, $S_A$, and $S_B$), and for any number of channels of the cochlear implant. For example, the clinician may determine the masking parameters ($X_A$, $X_B$, $S_A$, and $S_B$) for each individual channel of the cochlear implant, a number of channels, or determine universal parameters to be used across all channels. In further embodiments of the present invention, the fitting procedure may be used to determine the masking level described above with reference to FIG. 26.

In certain embodiments of the present invention, clinician 2764 causes fitting system 2766 to provide a first test signal 2772 to the recipient, which is delivered as an electrical stimulation via a first number of channels of the cochlear implant. Following deliver of this signal, the parameters within the recipient's cochlear implant, sometimes referred to as the recipient's MAP or MAP parameters, are adjusted and a second test signal 2772 is then delivered to the recipient. The recipient's MAP is adjusted such that the second test signal 2772 is delivered via more or less channels than the first test signal 2772. By evaluation the recipient's response to second test signal 2772, the clinican can determine if one or more delivered stimulation signals are masked. More specifically, if the recipient's response indicates that both the first and second test signals 2772 caused substantially the same or similar response, clincian 2764 may determine that the omitted signal was likely masked by one or more other signals. As such, this masking information is used by clinician 2764 to estimate the maskings effects and determine one or more of the masking parameters ($X_A$, $X_B$, $S_A$, and $S_B$). As would be appreciated, clinician 2764 may run a series of tests in which various signals are provided to the recipient to gather information regarding the masking effects of certain signals and/or channels.

In accordance with embodiments of the present invention, the recipient's response may comprise verbal or non-verbal feedback 2784 from recipient 2762. In such embodiments, using feedback 2784, clinician 2764 enters an indication of the recipient's response at a user interface using, for example, one or more control inputs 2770 such as any one or combination of known methods, including a computer keyboard, mouse, voice-responsive software, touch-screen, retinal control, joystick, and any other data entry or data presentation formats now or later developed. In alternative embodiments, the recipient's response may comprise objective measurements or speech scores, such as neural response measurements, obtained before, during or after delivery of electrical stimulation.

In further embodiments, the recipient may be provided with the ability to adjust or set one or more masking parameters ($X_A$, $X_B$, $S_A$, and $S_B$) and/or the masking level described above with reference to FIG. 26. In such embodiments, an external component of a cochlear implant, such as external component 2842 shown in FIG. 28, may include one or more user controls that permit the recipient to set/adjust the masking parameters and/or masking level.

Figure 28:
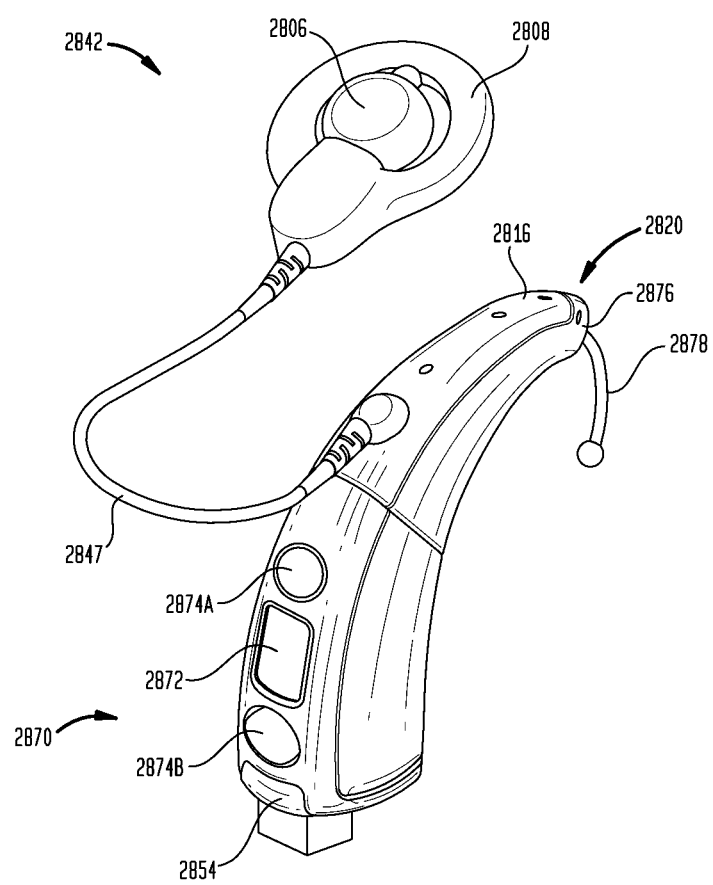
FIG. 28 is a perspective view of an exemplary external component of a cochlear implant in which embodiments of the present invention may be implemented.

As shown in FIG. 28, external component 2842 typically comprises a sound transducer 2820 for detecting sound, and for generating an electrical audio signal. In this illustrative embodiment, sound transducer 2820 is a microphone. In alternative embodiments, sound transducer 2820 may comprise, for example, more than one microphone, one or more telecoil induction pickup coils or other device now or later developed that may detect sound and generate electrical signals representative of such sound.

External component 2842 also comprises a signal processing unit 2816, a power source (not shown), and an external transmitter unit 2806. External transmitter unit 2806 comprises an external coil 2808 and, preferably, a magnet (not shown) secured directly or indirectly to the external coil 2808. Signal processing unit 2816 processes the output of microphone 2820 that is positioned, in the depicted embodiment, by outer ear 2801 of the recipient. Signal processing unit 2816 generates stimulation signals in accordance with the embodiments described above, and transmits coded signals to an internal component of the cochlear implant. These coded signals are provided to external transmitter unit 2806 via a cable 2847. Signal processing unit 2816 is, in this illustration, constructed and arranged so that it can fit behind outer ear 2801 in a BTE (behind-the-ear) configuration, but may also be worn on different parts of the recipient's body or clothing.

Also, as shown in FIG. 28, the external component includes a user interface 2870. User interface 2870 includes a display 2872 and control buttons 2874 which permit a recipient to set or adjust one or more masking parameters ($X_A$, $X_B$, $S_A$, and $S_B$) and/or the masking level described above. In some embodiments, display 2872 may display an indication of the masking level or any number of masking parameters. The recipient may then adjust the displayed parameters using control buttons 2874.

Referring specifically to embodiments in which a masking level as described above with reference to FIG. 26 is provided, display 2872 may display a number of pre-determined masking levels from which the user may select. These various masking levels may comprise default levels, clinician tuned levels, or levels that are designed to be used in a specific environment. In these embodiments, when a recipient enters a new sound environment, the user may select which of the various masking levels provides optimum speech understanding and comfort within that environment.

Although the above described embodiments were discussed with reference to a cochlear implant, in other embodiments these methods and systems may be used with other implant systems such as, for example, in an auditory brain stimulator or other tissue-stimulating prosthesis.

PCT application PCT/AU01/01032, filed Aug. 21, 2001, Australian Patent Application No. PQ9528 filed Aug. 21, 2000, U.S. Provisional Application No. 60/557,675, entitled "Spread of Excitation and MP3 Coding," filed Mar. 31, 2004, U.S. Provisional Application No. 60/616,216, entitled "Spread of Execution and Compressed Audible Speech Coding," filed Oct. 7, 2004, and U.S. patent application Ser. No. 11/857,253, filed Sep. 18, 2007, entitled "Power Efficient Electrical Stimulation," all of which are hereby incorporated by reference herein.

Further features and advantages of the present invention may be found in U.S. patent application Ser. No. 11/451,349, filed Jun. 13, 2006, entitled "Determining Stimulation Signals For Neural Coding," now pending, which is a continuation-in-part of U.S. application Ser. No. 11/094,769, filed Mar. 31, 2005, entitled "Compressed Neural Coding," now pending, which is a continuation-in-part of application Ser. No. 10/343,397, filed Feb. 21, 2003, entitled "Power Efficient Electrical Stimulation," now U.S. Pat. No. 7,272,446, which is a national stage of PCT application PCT/AU01/01032, filed Aug. 21, 2001, which claims priority to Australian Patent Application No. PQ9528 filed Aug. 21, 2000, as well as U.S. Provisional Application No. 60/557,675, entitled "Spread of Excitation and MP3 Coding," filed Mar. 31, 2004; and U.S. Provisional Application No. 60/616,216, entitled "Spread of Execution and Compressed Audible Speech Coding," filed Oct. 7, 2004, and commonly owned and co-pending U.S. patent application Ser. No. 11/857,253, filed Sep. 18, 2007, entitled "Power Efficient Electrical Stimulation," all of which are hereby incorporated by reference herein.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All documents, patents, journal articles and other materials cited in the present application are hereby incorporated by reference.

What is claimed is:

1. A method of providing neural stimulation to a recipient with a tissue-stimulating prosthesis having a plurality of channels for delivery of stimulation signals, comprising:
   receiving an input signal;
   identifying the perceptual power of frequency components of the input signal;
   generating stimulation signals corresponding to frequency components of said input signal;
   using the perceptual power of the frequency components of the input signal to select channels for delivery to the recipient of said generated stimulation signals; and
   delivering to the recipient said generated stimulation signals via said selected channels, wherein the input signal is received and said generated stimulation signals are generated prior to delivering said generated stimulation signals to the recipient.

2. The method of claim 1, wherein using the perceptual power of the frequency components of the input signal to select channels for delivery to the recipient of said generated stimulation signals comprises:
   determining a first frequency component having the largest perceptual power, said first frequency component corresponding to a first selected channel of the tissue-stimulating prosthesis; and
   deemphasizing one or more others channels of the tissue-stimulating prosthesis for delivery of stimulation signals.

3. The method of claim 2, wherein said first selected channel terminates in an electrode, and wherein said deemphasizing said plurality of channels comprises:
   deemphasizing a plurality of channels terminating in electrodes adjacent said first selected channel.

4. The method of claim 3, further comprising:
   deemphasizing channels terminating in electrodes positioned asymmetrically about said electrode of said first selected channel.

5. The method of claim 2, further comprising:
   deemphasizing channels terminating in electrodes positioned symmetrically about said electrode of said first selected channel.

6. The method of claim 5, wherein each of said plurality of deemphasized channels comprises channels having electrodes positioned on either side of, and immediately adjacent to said electrode of first selected channel.

7. The method of claim 2, wherein said deemphasizing said one or more channels comprises:
   deemphasizing said one or more channels using data determined during a fitting procedure.

8. The method of claim 2, wherein said deemphasizing said one or more channels comprises:

deemphasizing said one or more channels based on information indicative of a masking effect to be caused by delivery of one or more of the stimulation signals via the first selected channel.

9. The method of claim 2, wherein said deemphasizing said one or more channels further comprises:
adjusting which channels are to be masked based on an input by the recipient.

10. The method of claim 1, wherein using the perceptual power of the frequency components of the input signal to select channels for delivery to the recipient of said generated stimulation signals comprises:
assessing masking effects based on one or more psychophysical models of the human auditory system.

11. The method of claim 10, wherein said one or more psychophysical models comprise a psychoacoustic model.

12. The method of claim 10, wherein said one or more psychophysical models comprise a psychoelectric model.

13. The method of claim 10, wherein said one or more psychophysical models comprise a psychoacoustic model and a psychoelectric model.

14. The method of claim 1, wherein identifying the perceptual power of frequency components of the input signal comprises:
applying a pre-filter to the frequency components of the input signal that approximates an equal loudness function.

15. The method of claim 14, wherein the pre-filter is configured to compensate for varying thresholds-in-quiet at different frequencies.

16. A tissue-stimulating prosthesis for providing neural stimulation to a recipient comprising:
a sound input configured to receive an input signal;
a stimulation signal determination module configured to:
identify the perceptual power of frequency components of the input signal;
generate stimulation signals corresponding to frequency component of said input signal,
use the perceptual power of the frequency components of the input signal to select channels for delivery to the recipient of said generated stimulation signals; and
a stimulator unit configured to deliver to the recipient said generated stimulation signals via said selected channels, wherein the input signal is received and said generated stimulation signals are generated prior to delivering said generated stimulation signals to the recipient.

17. The prosthesis of claim 16, wherein to use the perceptual power of the frequency components of the input signal to select channels for delivery to the recipient of said generated stimulation signals, the stimulation signal determination module is configured to:
determine a first frequency component having the largest perceptual power, said first frequency component corresponding to a first selected channel of the tissue-stimulating prosthesis, and to deemphasize one or more others channels of the tissue-stimulating prosthesis for delivery of stimulation signals.

18. The prosthesis of claim 17, wherein said first selected channel terminates in an electrode, and wherein said prosthesis is further configured to deemphasize a plurality of channels terminating in electrodes adjacent said first selected channel.

19. The prosthesis of claim 18, wherein said stimulation signal determination module is further configured to deemphasize channels having electrodes positioned symmetrically about said electrode of said first selected channel.

20. The prosthesis of claim 19, wherein said stimulation signal determination module is further configured to deemphasize channels terminating in electrodes positioned on either side and immediately adjacent to said electrode of first selected channel.

21. The prosthesis of claim 18, wherein said stimulation signal determination module is further configured to deemphasize channels terminating in electrodes positioned asymmetrically about said electrode of said first selected channel.

22. The prosthesis of claim 18, wherein said stimulation signal determination module is further configured to deemphasize said channels based on a fitting procedure.

23. The prosthesis of claim 17, said stimulation signal determination module is further configured to deemphasize said channels based on information indicative of a masking effect to be cause by delivery of one or more of the stimulation signals via the first selected channel.

24. The prosthesis of claim 17, further comprising:
an interface configured to receive an input from the recipient, and
wherein the stimulation signal determination module is further configured to deemphasize said channels based on the input.

25. The prosthesis of claim 16, wherein to use the perceptual power of the frequency components of the input signal to select channels for delivery to the recipient of said generated stimulation signals, the stimulation signal determination module is configured to:
assess masking effects based on one or more psychophysical models of the human auditory system.

26. The prosthesis of claim 25, wherein said one or more psychophysical models comprise a psychoacoustic model.

27. The prosthesis of claim 25, wherein said one or more psychophysical models comprises a psychoelectric model.

28. The prosthesis of claim 25, wherein said one or more psychophysical models comprise a psychoacoustic model and a psychoelectric model.

29. The method of claim 16, wherein to identify the perceptual power of frequency components of the input signal the stimulation signal determination module is configured to:
apply a pre-filter to the frequency components of the input signal that approximates an equal loudness function.

30. The method of claim 29, wherein the pre-filter is configured to compensate for varying thresholds-in-quiet at different frequencies.

* * * * *